(12) United States Patent
Sasikumar et al.

(10) Patent No.: US 9,096,642 B2
(45) Date of Patent: Aug. 4, 2015

(54) THERAPEUTIC COMPOUNDS FOR IMMUNOMODULATION

(75) Inventors: Pottayil G. N. Sasikumar, Bangalore (IN); Muralidhara Ramachandra, Bangalore (IN); Suresh Kumar Vadlamani, Bangalore (IN); K. Rajeev Shrimali, Hyderabad (IN); Krishnaprasad Subbarao, Bangalore (IN)

(73) Assignee: Aurigene Discovery Technologies Limited, Bangalore (IN)

( * ) Notice: Subject to any disclaimer, the term of this patent is extended or adjusted under 35 U.S.C. 154(b) by 0 days.

(21) Appl. No.: 14/124,370

(22) PCT Filed: Dec. 21, 2011

(86) PCT No.: PCT/IN2011/000881
§ 371 (c)(1),
(2), (4) Date: Dec. 6, 2013

(87) PCT Pub. No.: WO2012/168944
PCT Pub. Date: Dec. 13, 2012

(65) Prior Publication Data
US 2014/0199334 A1    Jul. 17, 2014

Related U.S. Application Data

(60) Provisional application No. 61/515,007, filed on Aug. 4, 2011.

(30) Foreign Application Priority Data

Jun. 8, 2011   (IN) .......................... 1943/CHE/2011

(51) Int. Cl.
| C07K 7/02 | (2006.01) |
| C07K 5/02 | (2006.01) |
| A61K 38/08 | (2006.01) |
| A61K 38/00 | (2006.01) |

(52) U.S. Cl.
CPC . *C07K 7/02* (2013.01); *A61K 38/08* (2013.01); *C07K 5/0227* (2013.01); *A61K 38/00* (2013.01)

(58) Field of Classification Search
CPC ....................................................... C07K 7/02
See application file for complete search history.

(56) References Cited

U.S. PATENT DOCUMENTS

| 5,629,204 | A | 5/1997 | Honjo et al. |
| 6,808,710 | B1 | 10/2004 | Wood et al. |
| 6,936,704 | B1 | 8/2005 | Freeman et al. |
| 7,038,013 | B2 | 5/2006 | Freeman et al. |
| 7,432,059 | B2 | 10/2008 | Freeman et al. |
| 7,432,351 | B1 | 10/2008 | Chen |
| 7,709,214 | B2 | 5/2010 | Freeman et al. |
| 2009/0305950 | A1 | 12/2009 | Minato et al. |
| 2013/0330335 | A1* | 12/2013 | Bremel et al. ............. 424/134.1 |

FOREIGN PATENT DOCUMENTS

| WO | 0114557 A1 | 3/2001 | |
| WO | 0139722 A2 | 6/2001 | |
| WO | 0200730 A2 | 1/2002 | |
| WO | 0279499 A1 | 10/2002 | |
| WO | 0286083 A2 | 10/2002 | |
| WO | 03042402 A2 | 5/2003 | |
| WO | 2004004771 A1 | 1/2004 | |
| WO | 2004056875 A1 | 7/2004 | |
| WO | WO 2006/077601 | * 7/2006 | ............. A61M 5/315 |
| WO | 2007005874 A2 | 1/2007 | |
| WO | 2010027423 A2 | 3/2010 | |
| WO | 2010063011 A2 | 6/2010 | |
| WO | 2011161699 A2 | 12/2011 | |

OTHER PUBLICATIONS

Shinohara, T et al., Structure and chromosomal localization of human PD-1 gene (PDCD-1); Genomics 1994, vol. 23(3), pp. 704-706.
Agata, Y et al., Expression of the PD-1 antigen on the surface of stimulated mouse T and B lymphocytes; International Immunology 1996, vol. 8(5), p. 765.
Freeman, GJ et al., Engagement of the PD-1 immunoinhibitory receptor by a novel B7 family member leads to negative regulation of lymphocyte activation; Journal of Experimental Medicine 2000, vol. 192(7), pp. 1027-1034.
Latchman, Y et al., PD-L2 is a second ligand for PD-1 and inhibits T cell activation; Nature Immunology 2001, vol. 2(3), pp. 261-267.
Iwai, Y et al., PNAS 2002, vol. 99(19), pp. 12293-12297.
Blank, C et al., PD-L1/B7H-1 Inhibits the effector phase of tumor rejection by T cell receptor (TCR) transgenic CD8+ T cells; Cancer Research 2004, vol. 64, pp. 1140-1145.
Prokunina, L et al., A regulatory polymorphism in PDCD 1 is associated with susceptibility to systemic lupus erythematosus in humans; Nature Genetics 2002, vol. 32(4), pp. 666-669.
Nishimura, H et al., Immunological studies on PD-1 deficient mice: implication of PD-1 as a negative regulator for B-cell responses; International Immunology 1998, vol. 10(10), pp. 1563-1572.
Nishimura, H et al, Development of lupus-like autoimmune diseases by disruption of the PD-1 gene Encoding an ITIM motif-carrying immunoreceptor; Immunity 1999, vol. 11(2), pp. 141-151.

(Continued)

*Primary Examiner* — Amber D Steele
(74) *Attorney, Agent, or Firm* — Benjamin Aaron Adler

(57) ABSTRACT

The present invention provides Immunosuppressive compounds capable of inhibiting the programmed cell death 1 (PD1) signalling pathway. The present invention further provides peptide based compositions for treatment of cancer or treatment of infections via immunopotentiation caused by inhibition of immunosuppressive signalling induced by PD-1, PD-L1, or PD-L2 and therapies using them, immunopotentiative substrates included as the active ingredient. Further, the invention provides pharmaceutical compositions comprising the Immunosuppressive peptide compounds or modified peptide moieties for preventive and/or therapeutic agents for cancer, cancer metastasis, immunodeficiency, an infectious disease or the like and an application of PD-1 or PD-L1 as a testing or diagnostic agent or a research agent for such a disease.

20 Claims, 1 Drawing Sheet

(56) References Cited

OTHER PUBLICATIONS

Nishimura, H et al., Autoimmune dilated cardiomyopathy in PD-1 receptor-deficient mice Science 2001, vol. 291, pp. 319-332.
Finger, LR et al., The human PD-1 gene: complete cDNA, genomic organization, and developmentally regulated expression in B cell progenitors; Gene 1997, vol. 197(1-2), pp. 177-187.
Lazar-Molnar, E et al, Crystal structure of the complex between programmed death-1 (PD-1) and its ligand PD-L2;PNAS 2008, vol. 105(30), p. 10483-10488.
Lin Dyw et al., The PD-1/PDL-1 complex resembles the antigen-binding Fv domains of antibodies and the T cell receptors; PNAS 2008, vol. 105(9), pp. 3011-3016.

* cited by examiner

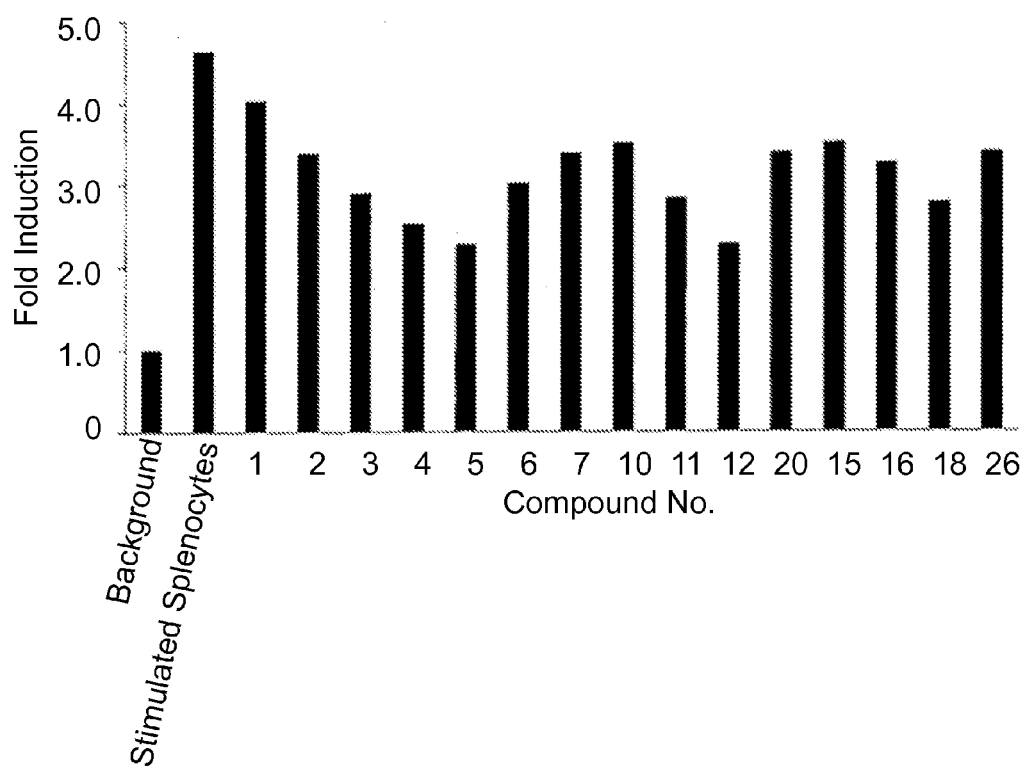

THERAPEUTIC COMPOUNDS FOR IMMUNOMODULATION

RELATED APPLICATION

This application claims the benefit of Indian provisional application number 1943/CHE/2011 filed on Jun. 8, 2011 and U.S. provisional application No. 61/515,007 filed on Aug. 4, 2011 all of which hereby incorporated by reference.

FIELD OF INVENTION

The present invention relates to novel peptides as therapeutic agents capable of inhibiting the programmed cell death 1 (PD1) signalling pathway.

The invention also relates to modifications and derivatives of the therapeutic agents.

The invention further relates to pharmaceutical compositions comprising the said novel peptides and their derivatives as therapeutic agents.

The invention also encompasses the use of the said therapeutic agents, modifications and derivatives for treatment of disorders via immunopotentiation comprising inhibition of immunosuppressive signal induced due to PD-1, PD-L1, or PD-L2 and therapies using them.

BACKGROUND OF THE INVENTION

Programmed Cell Death 1 or PD-1 (also referred to as PDCD1) is a ~55 kD type I membrane glycoprotein (Shinohara T et al, Genomics, 1994, Vol. 23, No. 3, 704-706). PD-1 is a receptor of the CD28 superfamily that negatively regulates T cell antigen receptor signalling by interacting with the specific ligands and is suggested to play a role in the maintenance of self tolerance.

PD-1 peptide relates to almost every aspect of immune responses including autoimmunity, tumour immunity, infectious immunity, transplantation immunity, allergy and immunological privilege.

The PD-1 protein's structure comprise of—
an extracellular IgV domain followed by
a transmembrane region and
an intracellular tail The intracellular tail contains two phosphorylation sites located in an immunoreceptor tyrosine-based inhibitory motif and an immunoreceptor tyrosine-based switch motif, which suggests that PD-1 negatively regulates TCR signals. Also, PD-1 is expressed on the surface of activated T cells, B cells, and macrophages, (Y. Agata et al., *Int Immunol, May* 1996, 8, 765.) suggesting that compared to CTLA-4 [(Cytotoxic T-Lymphocyte Antigen 4), also known as CD152 (Cluster of differentiation 152) is a protein that also plays an important regulatory role in the immune system], PD-1 more broadly negatively regulates immune responses.

PD-1 has two ligands, PD-L1 (Programmed Death Ligand 1 or PDCD1L1 or B7-H1) (Freeman G J et al, Journal of Experimental Medicine, 2000, Vol. 19, No. 7, 1027-1034.) and PD-L2 (Programmed Death Ligand 2 or PDCD1L2 or B7-DC) (Latchman Y et al, Nature Immunology, 2001, Vol. 2, No. 3, 261-267.), which are members of the B7 family. PD-L1 is known to be expressed not only in immune cells, but also in certain kinds of tumour cell lines (such as monocytic leukaemia-derived cell lines, mast cell tumour-derived cell lines, hematoma-derived cell lines, neuroblastoma-derived cell lines, and various mammary tumour-derived cell lines) and in cancer cells derived from diverse human cancer tissues (Latchman Y et al, Nature Immunology, 2001, Vol. 2, No. 3, 261-267.) and on almost all murine tumour cell lines, including PA1 myeloma, P815 mastocytoma, and B16 melanoma upon treatment with IFN-γ (Y. Iwai et al., *Proc Natl Acad Sci USA*, Sep. 17, 2002, 99, 12293. and C. Blank et al., *Cancer Res*, February 2004, 64, 1140.). Similarly PD-L2 expression is more restricted and is expressed mainly by dendritic cells and a few tumour cell lines. PD-L2 expression has been verified in Hodgkin's lymphoma cell lines and others. There is a hypothesis that some of the cancer or tumour cells take advantage from interaction between PD-1 and PD-L1 or PD-L2, for suppressing or intercepting T-cell immune responses to their own (Iwai Y et al, Proceedings of the National Academy of Science of the United States of America, 2002, Vol. 99, No. 19, 12293-12297.).

Tumour cells and virus (including HCV and HIV) infected cells are known to express the ligand for PD-1 (to create Immunosuppression) in order to escape immune surveillance by host T cells. It has been reported that the PD-1 gene is one of genes responsible for autoimmune diseases like systemic lupus erythematosus (Prokunina et al, Nature Genetics, 2002, Vol. 32, No. 4, 666-669.). It has also been indicated that PD-1 serves as a regulatory factor for the onset of autoimmune diseases, particularly for peripheral self-tolerance, on the ground that PD-1-deficient mice develop lupus autoimmune diseases, such as glomerulonephritis and arthritis (Nishimura H et al, International Immunology, 1998, Vol. 10, No. 10, 1563-1572; Nishimura H et al, Immunity, 1999, Vol. 11, No. 2, 141-151.), and dilated cardiomyopathy-like disease (Nishimura H et al, Science, 2001, Vol. 291, No. 5502, 319-332.).

Hence, in one approach, blocking the interaction of PD-1 with its ligand (PD-L1, PD-L2 or both) may provide an effective way for specific tumour and viral immunotherapy.

Wood et al in U.S. Pat. No. 6,808,710 discloses method for downmodulating an immune response comprising contacting an immune cell expressing PD-1 with an antibody that binds to PD-1, in multivalent form, such that a negative signal is transduced via PD-1 to thereby down modulate the immune response. Such an antibody may be a cross-linked antibody to PD-1 or an immobilized antibody to PD-1.

Freeman et al in U.S. Pat. No. 6,936,704 and its divisional patent U.S. Pat. No. 7,038,013 discloses isolated nucleic acids molecules, designated B7-4 nucleic acid molecules, which encode novel B7-4 polypeptides, isolated B7-4 proteins, fusion proteins, antigenic peptides and anti-B7-4 antibodies, which co-stimulates T cell proliferation in vitro when the polypeptide is present on a first surface and an antigen or a polyclonal activator that transmits an activating signal via the T-cell receptor is present on a second, different surface.

There are some reports regarding substances inhibiting immunosuppressive activity of PD-1, promoting or inhibiting the interaction between PD-1 and PD-L1 or PD-L2, as well as the uses thereof. PD-1, PD-L1 or PD-L2 inhibitory antibody, nucleic acid molecules or polypeptides are reported in WO200114557, WO2004004771, WO2004056875, WO2002079499, WO2003042402, WO2002086083, WO2001039722, WO2003042402 and WO200200730.

WO2007005874 describes isolated human monoclonal antibodies that specifically bind to PD-L1 with high affinity. The disclosure provides methods for treating various diseases including cancer using anti-PD-L1 antibodies.

US20090305950 describes multimers, particularly tetramers of an extracellular domain of PD-1 or PD-L1. U.S. Pat. Nos. 7,432,059 and 7,709,214 disclose isolated nucleic acids molecules, designated PD L2 nucleic acid molecules which encode novel B7 related molecules which are ligands for PD 1.

Despite existence of many disclosures as discussed above, however, a significant unmet medical need still exists due to the lack of effective peptides or modified peptides as therapeutic agents as alternatives in the therapeutic area. It is known that synthetic peptides offer certain advantages over antibodies such as ease of production with newer technologies, better purity and lack of contamination by cellular materials, low immunogenicity, improved potency and specificity. Peptides may be more stable and offer better storage properties than antibodies. Moreover, often peptides possess better tissue penetration in comparison with antibodies, which could result in better efficacy. Peptides can also offer definite advantages over small molecule therapeutics counterparts such as lesser degree of toxicity and lower probability of drug-drug interaction.

The present invention therefore may provide the solution for this unmet medical need by offering novel synthetic peptide and its derivatives which are based on the PD1 ectodomain.

BRIEF DESCRIPTION OF ACCOMPANYING DRAWINGS

FIG. 1 shows the effect of compounds on mouse splenocyte proliferation inhibited by PD1-PDL1 interaction in the presence of human breast carcinoma cell line, MDA-MB-231 over expressing PDL1.

AMINO ACID SEQUENCE INFORMATION

SEQ ID NO: 1 shows amino acid sequence of extracellular domain of human PD-1.
SEQ ID NO: 2 shows amino acid sequence of BC Loop.

SUMMARY OF INVENTION

In accordance with the present invention, novel modified peptides are provided which are capable of suppressing and/or inhibiting the programmed cell death 1 (PD1) signalling pathway.

In one aspect, the invention provides a modified peptide of formula (I):

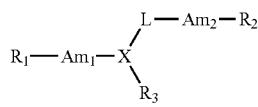

wherein, $Am_1$ represents 1 to 4 amino acid residues which may be same or different and each independently selected from Ser, Asn and Thr; wherein one of the peptide bond (—CONH—) between any two amino acid residues may be replaced with a modified peptide bond of

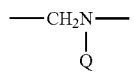

wherein Q is hydrogen, —CO($C_1$-$C_{20}$)alkyl or —COO($C_1$-$C_{20}$)alkyl;

$Am_2$ is comprising of dipeptide selected from Ser-Phe or Phe-Ser, wherein Phe may be optionally substituted with amino($C_1$-$C_{20}$)alkyl, —NHCOCH$_3$ or —NHCONH$_2$;

X is Glu which may optionally form amide bonds with its alpha carboxylic acid group, delta carboxylic acid group or amino group;

L is a linker selected from —NH(CH$_2$)$_n$NH—, —NH(CH$_2$)$_n$CH(NH$_2$)CO—, —OOC(CH$_2$)$_m$COO—, —NH(CH$_2$)$_n$CO—, —NH(CH$_2$CH$_2$O)$_n$NH—, —NH(CH$_2$CH$_2$O)$_n$CO— or —CO(CH$_2$CH$_2$O)$_n$CO—;

$R_1$ is free C-terminal, amidated C-terminal or N-terminal of $Am_1$; or is ($C_1$-$C_{20}$)acyl substitution;

$R_2$ is free C-terminal, amidated C-terminal or N-terminal of $Am_2$; or Y—$R_5$;

Y is an optional linker selected from —OOC(CH$_2$)$_m$COO—, —CO(CH$_2$)$_n$NH—, —CO(CH$_2$CH$_2$O)$_n$NH— or —COCH$_2$(OCH$_2$CH$_2$)$_n$NH—;

$R_5$ is an albumin binding moiety such as maleimido propionic acid;

$R_3$ is free alpha C-terminal, amidated alpha C-terminal or N-terminal of Glu;

'n' is an integer selected from 2 to 10, both inclusive;
'm' is an integer selected from 0 to 8, both inclusive;
or its retro analogue or a pharmaceutically acceptable stereoisomer or a pharmaceutically acceptable salt thereof.

In another aspect, the invention provides a modified peptide of formula (Ia):

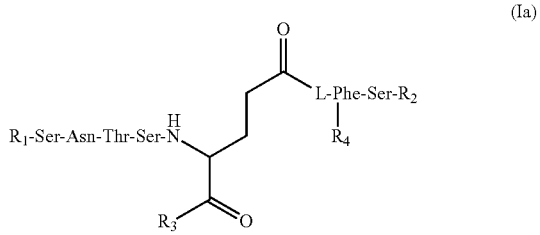

wherein,
$R_1$ is N-terminal of Ser; or ($C_1$-$C_{20}$)acyl substituted with either hydroxyl group or amino group of Ser L is a linker selected from —NH(CH$_2$)$_n$NH—, —NH(CH$_2$)$_n$CH(NH$_2$)CO—, —OOC(CH$_2$)$_m$COO—, —NH(CH$_2$)$_n$CO—, —NH(CH$_2$CH$_2$O)$_n$NH—, —NH(CH$_2$CH$_2$O)$_n$CO— or —CO(CH$_2$CH$_2$O)$_n$CO—;

$R_2$ is free C-terminal, amidated C-terminal or N-terminal of $Am_2$; or Y—$R_5$;

Y is an optional linker selected from —OOC(CH$_2$)$_m$COO—, —CO(CH$_2$)$_n$NH—, —CO(CH$_2$CH$_2$O)$_n$NH— or —COCH$_2$(OCH$_2$CH$_2$)$_n$NH—;

$R_5$ is an albumin binding moiety such as maleimido propionic acid;

$R_3$ is OH or NH$_2$;

$R_4$ is a substituent on phenyl group of Phe and is selected from hydrogen, amino($C_1$-$C_{20}$)alkyl, —NHCOCH$_3$ or —NHCONH$_2$;

'n' is an integer having values selected from 2 to 10, both inclusive;

'm' is an integer having values selected from 0 to 8, both inclusive; and one of the peptide bond (—CONH—) of Ser-Asn, Asn-Thr or Thr-Ser may be replaced with a modified peptide bond of

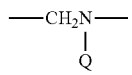

wherein Q is hydrogen, —CO($C_1$-$C_{20}$)alkyl or —COO($C_1$-$C_{20}$)alkyl group;

or retro analogue or a pharmaceutically acceptable stereoisomer or a pharmaceutically acceptable salt thereof.

In yet another aspect, the invention provides a modified peptide of formula (Ib):

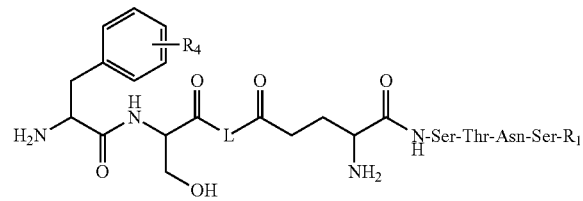

wherein,
R₁ is free C-terminal or amidated C-terminal of Ser;
L is a linker selected from —NH(CH₂)ₙNH— or —NH(CH₂CH₂O)ₙNH—;
R₄ is selected from hydrogen, amino(C₁-C₂₀)alkyl, —NHCOCH₃ or —NHCONH₂;
or retro analogue or a pharmaceutically acceptable stereoisomer or a pharmaceutically acceptable salt thereof

DETAILED DESCRIPTION OF THE INVENTION

The term 'peptide' is used herein to designate a sequence of natural or unnatural amino acids bonded in said sequence by peptide bonds.

The term 'compound(s)' as used herein comprises peptides and modified peptides as disclosed in the present invention.

The following common abbreviations of the amino acids are used throughout this specification:

| | | |
|---|---|---|
| Gly (or G)—glycine | Ala (or A)—alanine | Val (or V)—valine |
| Leu (or L)—leucine | Ile (or I)—isoleucine | Orn—ornithine |
| Pro (or P)—proline | Phe (or F)—phenylalanine | Trp (or W)—tryptophan |
| Met (or M)—methionine | Ser (or S)—serine | Thr (or T)—threonine |
| Cys (or C)—cysteine | Tyr (or Y)—tyrosine | Asn (or N)—asparagine |
| Gln (or Q)—glutamine | Asp (or D)—aspartic acid | Glu (or E)—glutamic acid |
| Lys (or K)—lysine | Arg (or R)—arginine | His (or H)—histidine |

The term "(C₁-C₂₀)alkyl" as used herein refers to straight or branched chain hydrocarbon having 1 to 20 carbon atoms including, but not limited to, methyl, ethyl, propyl, butyl, isobutyl and the like.

The term "amino(C₁-C₂₀)alkyl" as used herein refers to straight or branched chain hydrocarbon having 1 to 20 carbon atoms with an amino group including, but not limited to, aminomethyl, aminoethyl and the like.

The term "(C₁-C₂₀)acyl" as used herein refers to RC(O)—, wherein R is (C₁-C₂₀)alkyl as defined above. For example, acetyl, —C(O)(CH₂)₄CH₃, —C(O)(CH₂)₁₄CH₃ and the like.

The term "peptide bond" as used herein refers to the chemical bond between carbon and nitrogen in the bivalent group CONH that unites amino acid residues in a peptide.

The term "retro analogue" as used herein refers to a sequence of amino acids that has been altered with respect to a native amino acid sequence by the reversal of the direction of the native amino acid sequence. For example, for a native sequence "Ser-Asn-Thr-Ser"; the retro sequence would be "Ser-Thr-Asn-Ser". The retro analogue may be partial retro sequence.

The term "partial retro sequence" as used herein refers to a sequence of amino acids that has been partially altered with respect to a native amino acid sequence by the reversal of the direction of the native amino acid sequence. For example, for a native sequence "Ser-Asn-Thr-Ser-Glu-Phe-Ser"; the partial retro sequence would be "Phe-Ser-Glu-Ser-Thr-Asn-Ser".

The term "albumin binding moiety" as used herein refers to the moiety capable of binding to a serum albumin of a mammal which may alternatively, be an organic, non-proteinaceous compound with affinity for the mammalian serum albumin. The moiety is preferably a radical of such an organic compound, which is covalently bound to the biologically active protein moiety. For example, maleimido propionic acid, maleimidocaproic acid hydrazide (commonly referred to as EMCH) and the like.

The present invention provides immunosuppression modulating peptides capable of suppressing and/or inhibiting the programmed cell death 1 (PD1) signalling pathway.

The present invention further provides modifications, derivatives of the peptides and pharmaceutical compositions comprising the peptides for treatment of cancer or infection via immunopotentiation caused by inhibition of immunosuppressive signal induced by PD-1, PD-L1, or PD-L2 and therapies using them, immunopotentiative substrates included as the active ingredients.

In accordance with the present invention, in one of the embodiment there are provided compounds capable of inhibiting ability to inhibit the programmed cell death 1 (PD1) signalling pathway and being capable of reducing PD-L1 or PD-L2 binding to PD-1 and resulting immunosuppressive signalling by PD-1, wherein the compound comprises a peptide moiety or a modified peptide moiety.

The complete amino acid sequence of human PD-1 is disclosed in U.S. Pat. No. 5,629,204 (Honjo et. al.) and Finger et al., (Gene, 1997, 197, 177-187.). Human and mouse PD-1 share around 60% amino acid identity, whereas the extracellular IgV domain shows only 21% and 16% sequence identity with CD28 and CTLA4, respectively.

PD-1 possesses an ectodomain having multiple loop structures and strands between the loops. The amino acid sequence of the human PD-1 ectodomain is as set forth in SEQ ID NO: 1.

```
Extracellular domain of human PD-1
                                        SEQ ID NO: 1
PPTFSPALLVVTEGDNATFTCSFSNTSESFVLNWYRMSPSNQTDKLAAF

PEDRSQPGQDCRFRVTQLPNGRDFHMSVVRARRNDSGTYLCGAISLAPK

AQIKESLRAELRVTERRAEVPTAHPSPSPRSAGQFQTLV
```

These loop and strand assignments of amino acids are based on the 1.8-Å-resolution structure of the murine PD-1/PD-L2 complex reported in Lazar-Molnar et al, (PNAS, 2008, 105, 30, 10483-10488.).

Out of the various loops and strands of the PD-1 ectodomain, BC loop (i.e. 24th to 30th amino acid of SEQ ID NO: 1) was taken up for further modification. The present invention provides compounds comprising of modified BC loop of extracellular domain of human PD-1.

```

Modifications of the peptides discussed herein where relevant include replacements of some or all of the L-amino acids by D-amino acids, bonding of amino acids at other than alpha amino groups, including at side chain amino or carboxylic groups, inclusion of non-peptide linkers between peptide sequences, deletion of one or more amino acids, cross-linking, lipidation, stapling, and PEGylation.

The compounds of the invention may comprise linear or branched peptides.

In one aspect, the invention provides a modified peptide of formula (I):

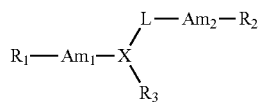
(I)

wherein, $Am_1$ represents 1 to 4 amino acid residues which may be same or different and each independently selected from Ser, Asn and Thr; wherein one of the peptide bond (—CONH—) between any two amino acid residues may be replaced with a modified peptide bond of

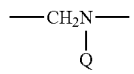

wherein Q is hydrogen, —CO($C_1$-$C_{20}$)alkyl or —COO($C_1$-$C_{20}$)alkyl;

$Am_2$ is comprising of dipeptide selected from Ser-Phe or Phe-Ser, wherein Phe may be optionally substituted with amino($C_1$-$C_{20}$)alkyl, —NHCOCH$_3$ or —NHCONH$_2$;

X is Glu which may optionally form amide bonds with its alpha carboxylic acid group, delta carboxylic acid group or amino group;

L is a linker selected from —NH(CH$_2$)$_n$NH—, —NH(CH$_2$)$_n$CH(NH$_2$)CO—, —OOC(CH$_2$)$_m$COO—, —NH(CH$_2$)$_n$CO—, —NH(CH$_2$CH$_2$O)$_n$NH—, —NH(CH$_2$CH$_2$O)$_n$CO— or —CO(CH$_2$CH$_2$O)$_n$CO—;

$R_1$ is free C-terminal, amidated C-terminal or N-terminal of $Am_1$; or is ($C_1$-$C_{20}$)acyl substitution;

$R_2$ is free C-terminal, amidated C-terminal or N-terminal of $Am_2$; or Y—$R_5$;

Y is an optional linker selected from —OOC(CH$_2$)$_m$COO—, —CO(CH$_2$)$_n$NH—, —CO(CH$_2$CH$_2$O)$_n$NH— or —COCH$_2$(OCH$_2$CH$_2$)$_n$NH—;

$R_5$ is an albumin binding moiety such as maleimido propionic acid;

$R_3$ is free alpha C-terminal, amidated alpha C-terminal or N-terminal of Glu;

'n' is an integer selected from 2 to 10, both inclusive;

'm' is an integer selected from 0 to 8, both inclusive;

or its retro analogue or a pharmaceutically acceptable stereoisomer or a pharmaceutically acceptable salt thereof In another aspect, the invention provides a modified peptide of formula (Ia):

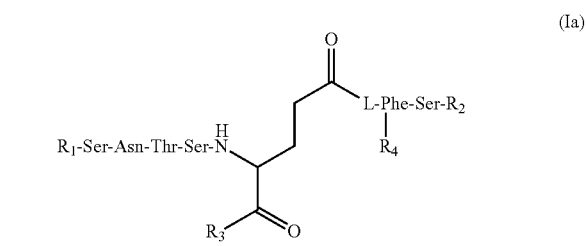
(Ia)

wherein, $R_1$ is N-terminal of Ser; or ($C_1$-$C_{20}$)acyl substituted with either hydroxyl group or amino group of Ser L is a linker selected from —NH(CH$_2$)$_n$NH—, —NH(CH$_2$)$_n$CH(NH$_2$)CO—, —OOC(CH$_2$)$_m$COO—, —NH(CH$_2$)$_n$CO—, —NH(CH$_2$CH$_2$O)$_n$NH—, —NH(CH$_2$CH$_2$O)$_n$CO— or —CO(CH$_2$CH$_2$O)$_n$CO—;

$R_2$ is free C-terminal, amidated C-terminal or N-terminal of $Am_2$; or Y—$R_5$;

Y is an optional linker selected from —OOC(CH$_2$)$_m$COO—, —CO(CH$_2$)$_n$NH—, —CO(CH$_2$CH$_2$O)$_n$NH— or —COCH$_2$(OCH$_2$CH$_2$)$_n$NH—;

$R_5$ is an albumin binding moiety such as maleimido propionic acid;

$R_3$ is OH or NH$_2$;

$R_4$ is a substituent on phenyl group of Phe and is selected from hydrogen, amino($C_1$-$C_{20}$)alkyl, —NHCOCH$_3$ or —NHCONH$_2$;

'n' is an integer having values selected from 2 to 10, both inclusive;

'm' is an integer having values selected from 0 to 8, both inclusive; and one of the peptide bond (—CONH—) of Ser-Asn, Asn-Thr or Thr-Ser may be replaced with a modified peptide bond of

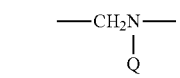

wherein Q is hydrogen, —CO($C_1$-$C_{20}$)alkyl or —COO($C_1$-$C_{20}$)alkyl group;

or retro analogue or a pharmaceutically acceptable stereoisomer or a pharmaceutically acceptable salt thereof In yet another aspect, the invention provides a modified peptide of formula (Ib):

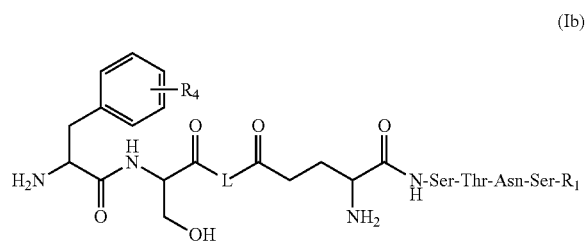
(Ib)

wherein, $R_1$ is free C-terminal or amidated C-terminal of Ser;

L is a linker selected from —NH(CH$_2$)$_n$NH— or —NH(CH$_2$CH$_2$O)$_n$NH—;

$R_4$ is selected from hydrogen, amino($C_1$-$C_{20}$)alkyl, —NHCOCH$_3$ or —NHCONH$_2$;

or retro analogue or a pharmaceutically acceptable stereoisomer or a pharmaceutically acceptable salt thereof The embodiment below are illustrative of the present invention and are not intended to limit the claims to the specific embodiments exemplified.

According to one embodiment, specifically provided are compounds of the formula (Ia) in which $R_1$ is N-terminal of $Am_1$.

According to another embodiment, specifically provided are compounds of the formula (Ia) in which $R_1$ is ($C_1$-$C_{20}$) acyl.

According to yet another embodiment, specifically provided are compounds of the formula (Ia) in which L is —NH(CH$_2$)$_n$NH— and 'n' is 4.

According to yet another embodiment, specifically provided are compounds of the formula (Ia) in which L is —NH(CH$_2$)$_n$CH(NH$_2$)CO— and 'n' is 4.

According to yet another embodiment, specifically provided are compounds of the formula (Ia) in which $R_2$ is N-terminal of $Am_2$.

According to yet another embodiment, specifically provided are compounds of the formula (Ia) in which $R_2$ is Y—$R_5$ wherein Y is absent and $R_5$ is maleimido propionic acid.

According to yet another embodiment, specifically provided are compounds of the formula (Ia) in which $R_2$ is Y—$R_5$ wherein Y is —COCH$_2$(OCH$_2$CH$_2$)$_n$NH—, 'n' is 2 and $R_5$ is maleimido propionic acid.

According to yet another embodiment, specifically provided are compounds of the formula (Ia) in which $R_4$ is hydrogen.

According to yet another embodiment, specifically provided are compounds of the formula (Ia) in which $R_4$ is aminoalkyl.

According to yet another embodiment, specifically provided are compounds of the formula (Ia) in which $R_4$ is —NHCOCH$_3$.

According to yet another embodiment, specifically provided are compounds of the formula (Ia) in which $R_4$ is —NHCONH$_2$.

According to yet another embodiment, specifically provided are compounds of the formula (Ia) in which the peptide bond (—CONH—) of Ser-Asn is replaced with a modified peptide bond of

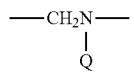

wherein Q is hydrogen, —CO($C_1$-$C_{20}$)alkyl or —COO($C_1$-$C_{20}$)alkyl group and the alkyl group may be linear or branched.

According to yet another embodiment, specifically provided are compounds of the formula (Ia) in which the peptide bond (—CONH—) of Asn-Thr is replaced with a modified peptide bond of

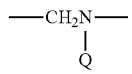

wherein Q is hydrogen, —CO($C_1$-$C_{20}$)alkyl or —COO($C_1$-$C_{20}$)alkyl group and the alkyl group may be linear or branched.

According to yet another embodiment, specifically provided are compounds of the formula (Ib) in which $R_1$ is amidated C-terminal of Ser.

According to yet another embodiment, specifically provided are compounds of the formula (Ib) in which L is —NH—(CH$_2$)$_n$—NH— and 'n' is 4.

According to yet another embodiment, specifically provided are compounds of the formula (Ib) in which $R_4$ is hydrogen.

According to yet another embodiment, specifically provided are compounds capable of suppressing and/or inhibiting the programmed cell death 1 (PD1) signalling pathway, wherein the structures of the compounds are provided in Table 1.

It should be understood that the formulas (I), (Ia) and (Ib) structurally encompasses all stereoisomers, enantiomers and diastereomers, and pharmaceutically acceptable salts that may be contemplated from the chemical structure of the genera described herein.

Compounds of the invention may comprise peptide moieties that are lipidated and/or are glycosylated. One or more of the amino acids of the peptide may be a D-amino acid with a view to increasing stability in vivo.

The invention includes compounds as described above, formulated for pharmaceutical administration, typically by combination with a pharmaceutically acceptable carrier or diluent.

The invention includes compounds as described above for use in a method of medical treatment, e.g. in the treatment of cancer, treatment of bacterial and viral infections The invention further includes a method of screening compounds for ability to block interaction between PD-1 and a PD-1 ligand, comprising contacting candidate compounds of the kind described above with PD-1 or a PD-1 ligand binding portion of PD-1 and with a PD-1 ligand or a PD-1 binding portion of a PD-1 ligand, and measuring the extent of PD-1/PD-1 ligand binding.

In addition, compounds of the invention may be combined with carrier molecules such as dendrimers, e.g. PAMAM dendrimers, liposomes, micro-particles and nanoparticles such as polycyanoacrylate nanoparticles, and these also may be PEGylated.

Below are the representative compounds, which are illustrative in nature only and are not intended to limit the scope of the invention.

TABLE 1
| Comp No. | Structure |
|---|---|
| 001 | 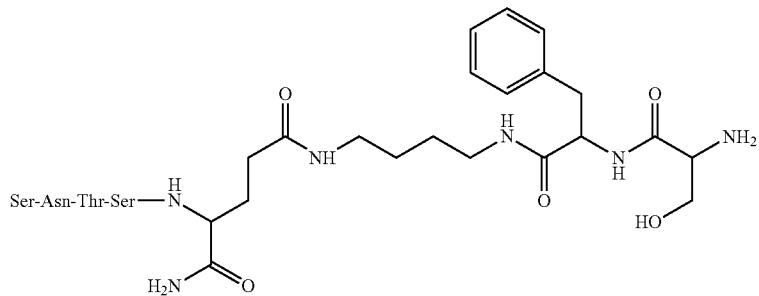<br>(SEQ ID NO: 3) |
| 002 | 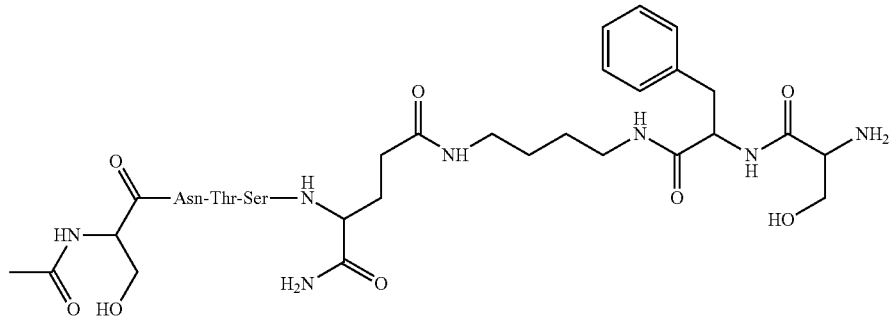<br>(SEQ ID NO: 4) |
| 003 | 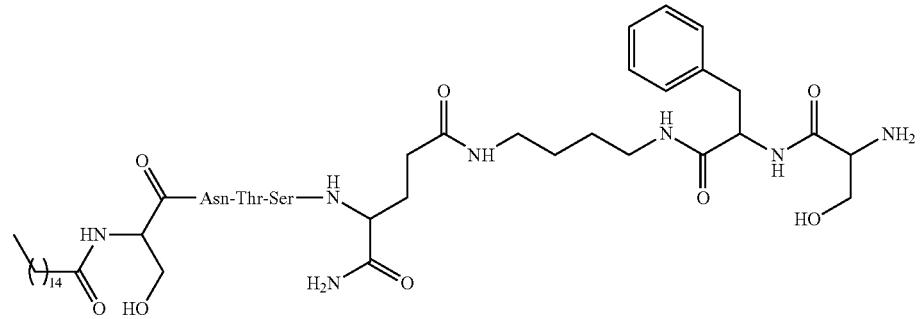<br>(SEQ ID NO: 5) |
| 004 | 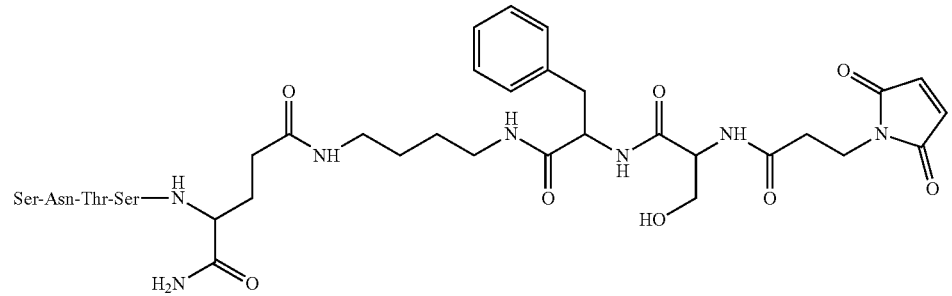<br>(SEQ ID NO: 6) |

TABLE 1-continued

| Comp No. | Structure |
|---|---|
| 005 | Ser-Asn-Thr-Ser—NH—[Glu(CONH(CH₂)₄NH-Phe-Ser-NH-CH₂-CH₂-O-CH₂-CH₂-O-CH₂-CH₂-NH-C(O)-CH₂-CH₂-maleimide)]-CONH₂ (SEQ ID NO: 7) |
| 006 | Ser-Asn-Thr-Ser—NH—[Glu(CONH(CH₂)₄NH-D-Phe-Ser)]-CONH₂ (SEQ ID NO: 8) |
| 007 | Ser-Asn-Thr-Ser—NH—[Glu(CONH(CH₂)₄NH-(4-aminomethyl)Phe-Ser-NH₂)]-CONH₂ (SEQ ID NO: 9) |
| 008 | D-Ser-Asn-Thr-Ser—NH—[Glu(CONH(CH₂)₄NH-Phe-Ser-NH₂)]-CONH₂ (SEQ ID NO: 10) |

TABLE 1-continued
| Comp No. | Structure |
|---|---|
| 009 | 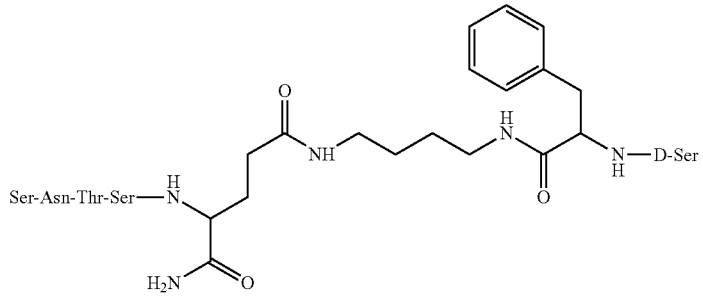<br>(SEQ ID NO: 11) |
| 010 | 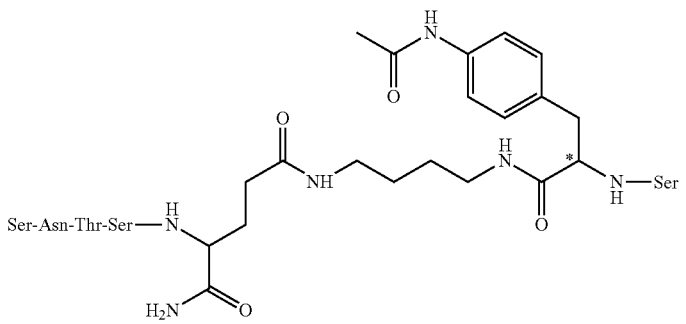<br>*D-Phe<br>(SEQ ID NO: 12) |
| 011 | 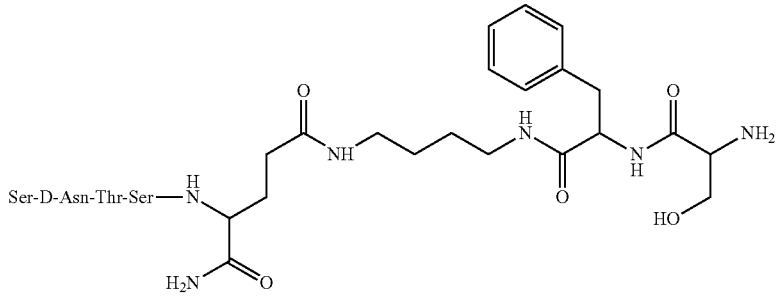<br>(SEQ ID NO: 13) |
| 012 | 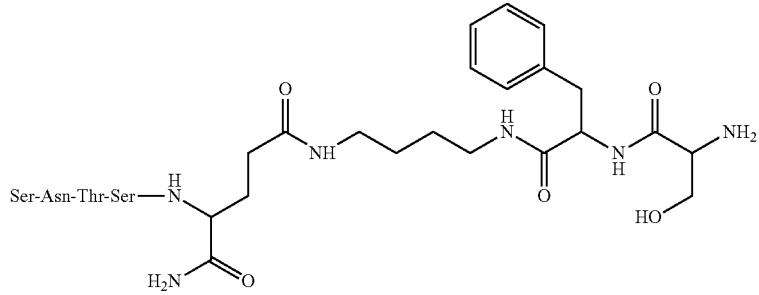<br>*D-Glu<br>(SEQ ID NO: 14) |

US 9,096,642 B2
TABLE 1-continued
| Comp No. | Structure |
|---|---|
| 013 | 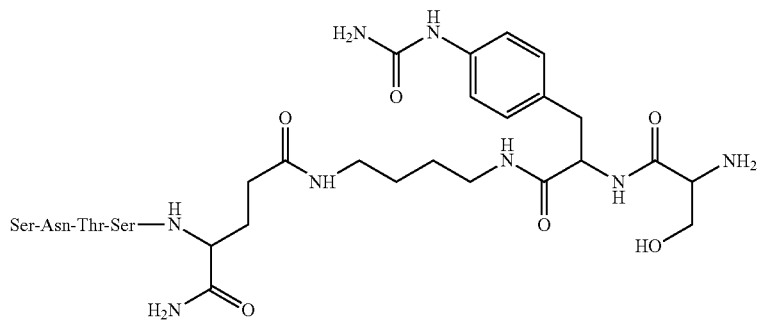  *D-Phe urea (SEQ ID NO: 15) |
| 014 | 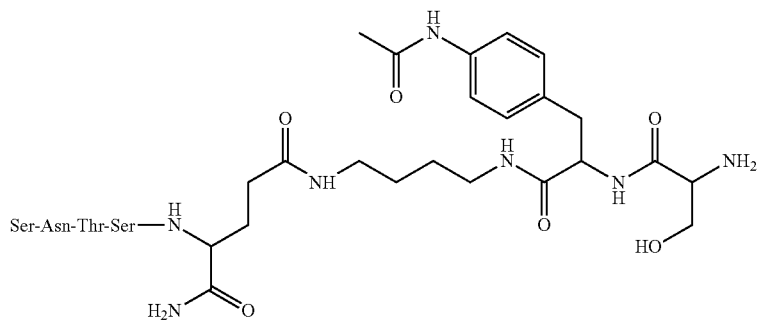  (SEQ ID NO: 16) |
| 015 | 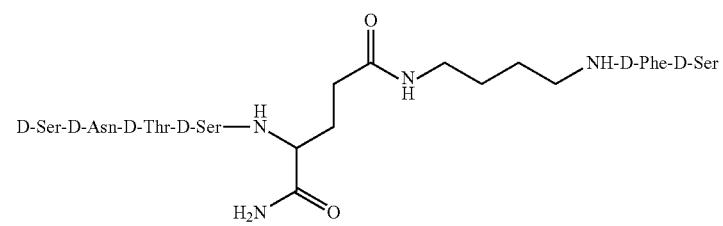  *D-Glu (SEQ ID NO: 17) |
| 016 | 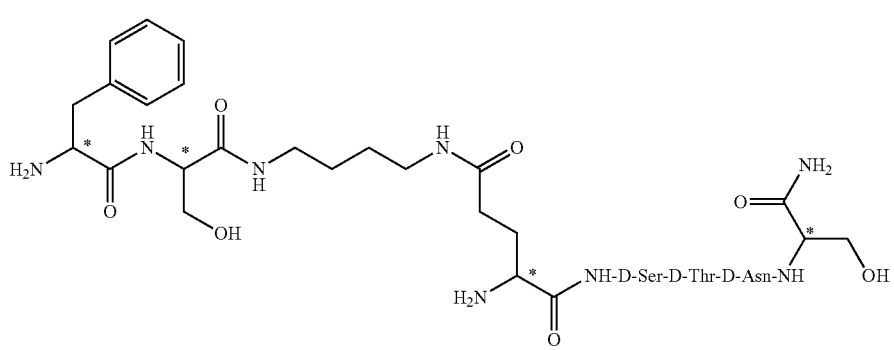  *All D-amino acids (SEQ ID NO: 18) |

TABLE 1-continued
| Comp No. | Structure |
|---|---|
| 017 | 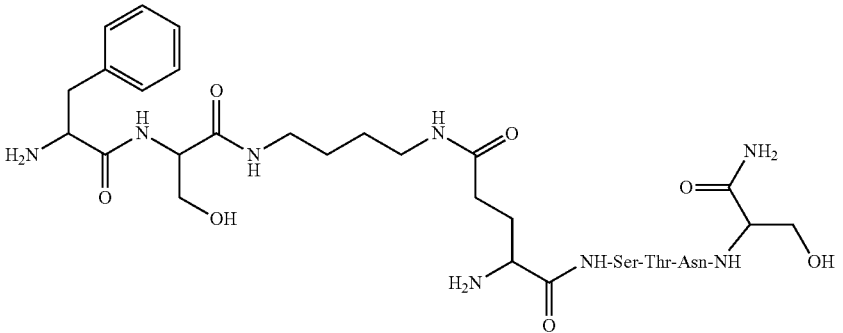<br>(SEQ ID NO: 19) |
| 018 | 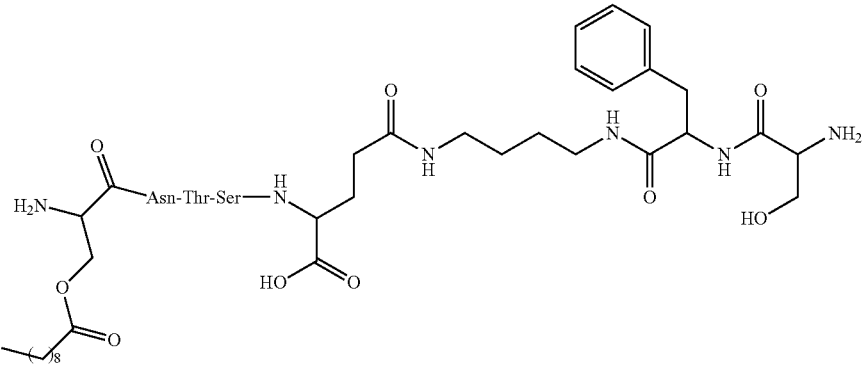<br>(SEQ ID NO: 20) |
| 019 | 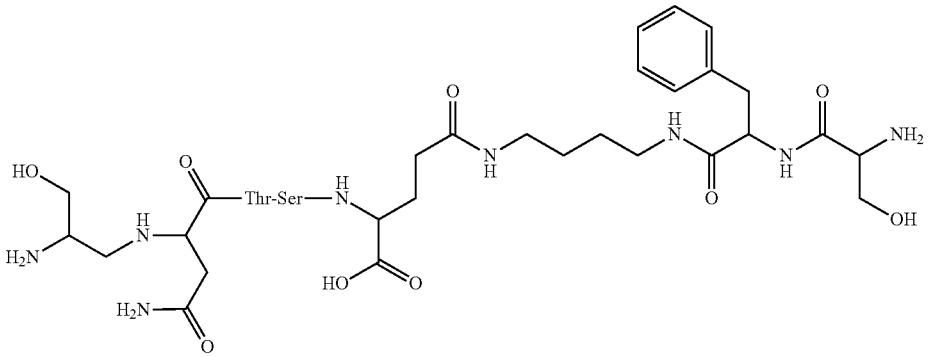<br>(SEQ ID NO: 21) |

TABLE 1-continued
| Comp No. | Structure |
|---|---|
| 020 | 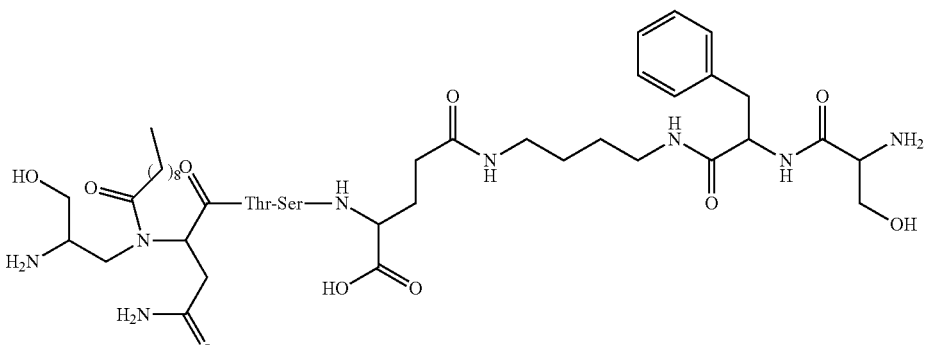<br>(SEQ ID NO: 22) |
| 021 | 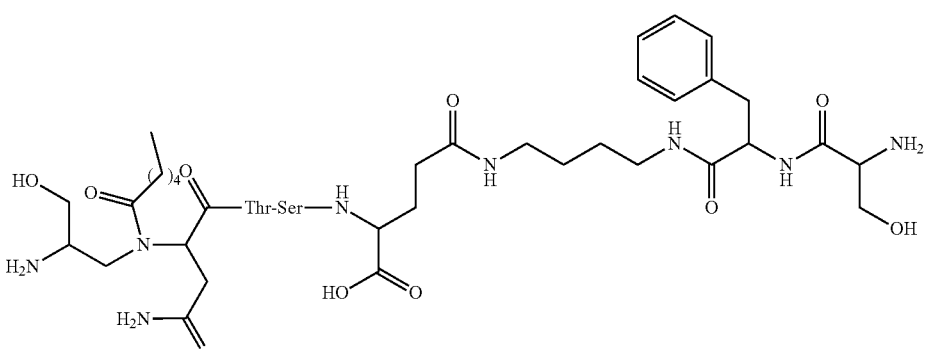<br>(SEQ ID NO: 23) |
| 022 | 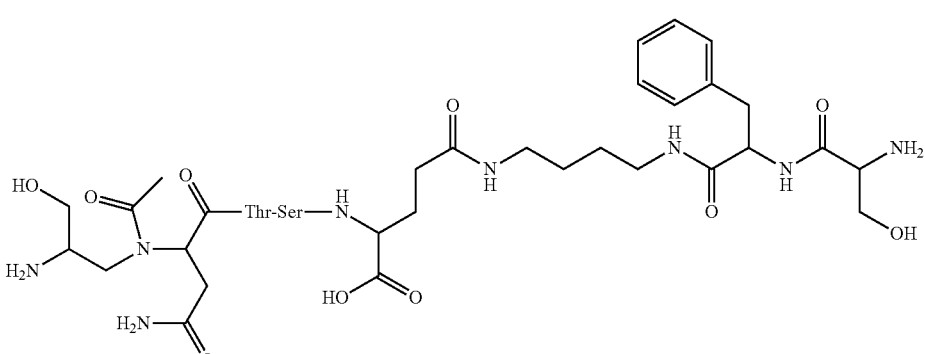<br>(SEQ ID NO: 24) |

TABLE 1-continued

| Comp No. | Structure |
|---|---|
| 023 | (SEQ ID NO: 25) |
| 024 | (SEQ ID NO: 26) |
| 025 | (SEQ ID NO: 27) |

TABLE 1-continued

| Comp No. | Structure |
|---|---|
| 026 | (SEQ ID NO: 28) |
| 027 | (SEQ ID NO: 29) |
| 028 | (SEQ ID NO: 30) |
| 029 | (SEQ ID NO: 31) |

TABLE 1-continued

| Comp No. | Structure |
|---|---|
| 030 | (structure with Thr-Ser linkage) (SEQ ID NO: 32) |
| 031 | (structure with Ser linkage) (SEQ ID NO: 33) |

In one of the embodiment of the present invention there is provided a compound having the ability to inhibit the programmed cell death 1 (PD1) signalling pathway and being capable of reducing PD-L1 or PD-L2 binding to PD-1 and resulting immunosuppressive signalling by PD-1.

Further embodiment of the present invention relates to the compounds as disclosed in the present invention, wherein one or more of the amino acids are substituted with D-amino acid.

The compounds as disclosed in the present invention are formulated for pharmaceutical administration.

Another embodiment of the present invention provided a pharmaceutical composition comprising the compound as disclosed, and a pharmaceutically acceptable carrier or diluent.

Yet another embodiment of the present invention provides use of the compounds as disclosed in the present invention for the preparation of a medicament for the treatment of cancer.

Yet another embodiment of the present invention provides use of the compounds as disclosed in the present invention for the preparation of a medicament for the treatment of bacterial, fungal and viral infection.

Yet another embodiment of the present invention provides a method of treatment of cancer, wherein the method comprises administration of an effective amount of the compound and/or peptides of the present invention to the subject in need thereof. Yet another embodiment of the present invention provides a method for inhibiting growth of tumour cells and/or metastasis by administering an effective amount of the compound of the present invention to the subject in need thereof The said tumour cells include cancer such as but not limited to melanoma, renal cancer, prostate cancer, breast cancer, colon cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumours of childhood, lymphocytic lymphoma, cancer of the bladder, cancer of the kidney or ureter, carcinoma of the renal pelvis, neoplasm of the central nervous system (CNS), primary CNS lymphoma, tumour angiogenesis, spinal axis tumour, brain stem glioma, pituitary adenoma, Kaposi's sarcoma, epidermoid cancer, squamous cell cancer, T-cell lymphoma, environmentally induced cancers including those induced by asbestos, and combinations of said cancers.

Yet another embodiment of the present invention provides a method of treatment of infection via immunopotentiation caused by inhibition of immunosuppressive signal induced by PD-1, PD-L1, or PD-L2, wherein the method comprises administration of an effective amount of the compound and/or peptides of the present invention to the subject in need thereof.

The infectious disease includes but not limited to HIV, Influenza, Herpes, *Giardia*, Malaria, *Leishmania*, the pathogenic infection by the virus Hepatitis (A, B, & C), herpes virus (e.g., VZV, HSV-I, HAV-6, HSV-II, CMV and Epstein Barr virus), adenovirus, influenza virus, flaviviruses, echovirus, rhinovirus, coxsackie virus, cornovirus, respiratory syncytial virus, mumps virus, rotavirus, measles virus, *rubella* virus, parvovirus, vaccinia virus, HTLV virus, dengue virus, papillomavirus, molluscum virus, poliovirus, rabies virus, JC virus and arboviral encephalitis virus, pathogenic infection by the bacteria *chlamydia*, rickettsial bacteria, mycobacteria, staphylococci, streptococci, pneumonococci, meningococci, conococci, *klebsiella, proteus, serratia, pseudomonas, E. coli, legionella*, diphtheria, salmonella, bacilli, cholera, tetanus, botulism, anthrax, plague, leptospirosis, and Lyme's disease bacteria, pathogenic infection by the fungi *Candida* (*albicans, krusei, glabrata, tropicalis*, etc.), *Cryptococcus neoformans, Aspergillus* (*fumigatus, niger*, etc.), Genus *Mucorales* (*mucor, absidia, rhizophus*), *Sporothrix schenkii, Blastomyces dermatitidis, Paracoccidioides brasiliensis, Coccidioides immitis* and *Histoplasma capsulatum* and pathogenic infection by the parasites *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi, Nippostrongylus brasiliensis*.

Still yet another embodiment of the present invention provides a method for treating sepsis in a subject comprising administering to the subject a therapeutically effective amount of compound of the present invention, capable of inhibiting the programmed cell death 1 (PD1) signaling pathway such that the subject is treated for the bacterial, fungal and viral infections.

The compounds of the present invention may be used as single drug or as a pharmaceutical composition in which the compound is mixed with various pharmacologically acceptable materials.

The pharmaceutical composition is usually administered by a parenteral administration route, but can be administered by oral or inhalation routes. Examples of the parenteral administration include administration by injection, and percutaneous, transmucosal, transnasal and transpulmonary administrations.

The injectable materials include a solution, a suspension, and a solid injection that is dissolved or suspended in a solvent before use.

The injection is used after one or more active ingredients are dissolved, suspended or emulsified in a solvent. Examples of the solvent include water-soluble solvents (e.g., distilled water, physiological saline and Ringer's solution), oil solvents (e.g., vegetable oils such as olive oil, sesame oil, cotton oil and corn oil, and alcohols such as propylene glycol, polyethylene glycol and ethanol), and combinations thereof.

Further, the injection may contain a stabilizer (e.g., human serum albumin), solubilizing agent (e.g., polyethylene glycol, propylene glycol, D-mannitol, trehalose, benzyl benzoate, ethanol, trisaminomethane, cholesterol, triethanolamine, sodium carbonate, sodium citrate, sodium salicylate and sodium acetate), suspending agent (e.g., surfactants such as stearyl triethanolamine, sodium lauryl sulfate, lauryl aminopropionic acid, lecithin, benzalkonium chloride, benzethonium chloride and glyceryl monostearate; hydrophilic polymers such as polyvinyl alcohol, polyvinyl pyrrolidone, sodium carboxymethyl cellulose, methyl cellulose, hydroxymethyl cellulose, hydroxyethyl cellulose and hydroxypropyl cellulose; polysorbates; and polyoxyethylene hardened castor oil), emulsifier, soothing agent (e.g., benzyl alcohol), tonicity agent (e.g., sodium chloride, glycerin, D-mannitol, D-sorbitol and glucose), buffer, preservative (e.g., methylparaben, propylparaben, benzyl alcohol, chlorobutanol and phenol), antiseptic (e.g., paraoxybenzoic esters, chlorobutanol, benzyl alcohol, phenethyl alcohol, dehydroacetic acid and sorbic acid), antioxidant (e.g., sulfite and ascorbate) and dispersant (e.g., Polysorbate 80, Polyoxyethylene hardened castor oil 60, ethylene glycol, carboxymethyl cellulose and sodium alginate).

These injections may be prepared by known methods in the formulation technology field, such as by a method described in various Pharmacopoeia. They are prepared, for example, through a sterilization process at the final stage, or by aseptic manipulation. It is also possible to use an aseptic solid formulation, such as a freeze dried product, wherein the aseptic solid formulation is prepared and dissolved in aseptic or sterilized distilled water for injection or other solvents before use.

These parenteral solutions may be supplied in a vessel with a standard capacity, such as a plastic or glass vial, ampoule, syringe and injector, or in a vessel with a large capacity, such as a bottle.

The dosage of the compounds of the present invention varies depending on age, weight, symptom, therapeutic efficacy, dosing regimen and/or treatment time. Generally, they may be administered by a parenteral route (preferably intravenous administration) in an amount of 1 mg to 100 mg per time, from once a couple of days, once 3 days, once 2 days, once a day to a couple of times a day, in the case of an adult, or continuously administered by intravenous administration from 1 to 24 hours a day. Since the dosage is affected by various conditions, an amount less than the above dosage may sometimes work well enough, or higher dosage may be required in some cases.

Parenteral administration by injection includes all forms of injections, and also includes intravenous fluids. For example, it includes intramuscular injections, subcutaneous injections, intradermal injections, intraarterial injections, intravenous injections, intraperitoneal injections, injections to spinal cavity, and intravenous drops.

The compounds of the present invention may be administered in combination with other drugs for (1) complementation and/or enhancement of prevention and/or therapeutic efficacy of the preventive and/or therapeutic drug of the present invention, (2) dynamics, absorption improvement, dosage reduction of the preventive and/or therapeutic drug of the present invention, and/or (3) reduction of the side effects of the preventive and/or therapeutic drug of the present invention.

A concomitant medicine comprising the peptide of the present invention and other drug may be administered as a combination preparation in which both components are contained in a single formulation, or administered as separate formulations. The administration by separate formulations includes simultaneous administration and administration with some time intervals. In the case of the administration with some time intervals, the compound of the present invention can be administered first, followed by another drug or another drug can be administered first, followed by the compound of the present invention. The administration method of the respective drugs may be the same or different.

The dosage of the other drug can be properly selected, based on a dosage that has been clinically used. The compounding ratio of the compound of the present invention and the other drug can be properly selected according to age and weight of a subject to be administered, administration method, administration time, disorder to be treated, symptom and combination thereof. For example, the other drug may be used in an amount of 0.01 to 100 parts by mass, based on 1 part by mass of the compound of the present invention. The other drug may be a combination of two or more kind of arbitrary drugs in a proper proportion. The other drug that complements and/or enhances the preventive and/or therapeutic efficacy of the compound of the present invention includes not only those that have already been discovered, but those that will be discovered in future, based on the above mechanism.

Diseases on which this concomitant use exerts a preventive and/or therapeutic effect are not particularly limited. The concomitant medicine can be used for any diseases, as long as it complements and/or enhances the preventive and/or therapeutic efficacy of the compound of the present invention.

Particularly, since the compound of the present invention exhibits an effect of stimulating or proliferating lymphoid cells, the concomitant use is able to reduce a dosage of chemotherapeutics commonly used or an irradiation dosage in radio therapy. This results in suppression of side effects that accompany with chemotherapy and radio therapy.

The compound of the present invention can be used with an existing chemotherapeutic concomitantly or in a mixture form. Examples of the chemotherapeutic include an alkylation agent, nitrosourea agent, antimetabolite, anticancer antibiotics, vegetable-origin alkaloid, topoisomerase inhibitor, hormone drug, hormone antagonist, aromatase inhibitor, P-glycoprotein inhibitor, platinum complex derivative, other immunotherapeutic drugs and other anticancer drugs. Further, it can be used with a cancer treatment adjunct, such as a leucopenia (neutrophenia) treatment drug, thrombocytopenia treatment drug, antiemetic and cancer pain intervention drug, concomitantly or in a mixture form.

The compound of the present invention can be used with other immunomodulators concomitantly or in a mixture form. Examples of the immunomodulator include various cytokines Examples of the cytokines that stimulates immune responses include GM-CSF, M-CSF, G-CSF, interferon-α, β, or γ, IL-1, IL-2, IL-3 and IL-12.

The concomitant use of the compound of the present invention and a cancer antigen is able to give an additive or synergetic enhancement effect. Examples of the cancer antigen include HLA-A1 and HLA-A2 derived peptides derived from MAGE-1 or MAGE-3 of malignant melanoma, MART-1 and gp100, HER2/neu peptide of breast cancer and ovarian cancer, MUC-1 peptide of adenocarcinoma and NY-ESO—1 of metastatic cancer.

EXPERIMENTAL

Purification and Characterization of Peptide

The Reverse phase analytical HPLC was performed using on Zorbax Eclipse XDB-C18 silica column (4.6 mm×250 mm, 5 μm). Buffer A: 0.1% TFA/Water, Buffer B: 0.1% TFA in 9:1 acetonitrile/water. Equilibration of the column with 2% buffer B and elution by a gradient of 2% to 25% buffer B in 5 min and from 25% to 40% buffer B in total run time of 20 min.

LCMS was performed on AP1 2000 LC/MS/MS triple quad (Applied biosystems) with Agilent 1100 series HPLC with G1315 B DAD diode array detector, using Mercury MS column.

For further illustration of methods of preparing the compounds of the present invention, the following examples are disclosed below.

Example 1

Synthesis of Compound 1 coupling was initiated with DIC (0.36 mL; 5 equiv) and HOBT (0.32 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. After the first amino acid attachment, the un-reacted amino group, if any, in the resin is capped, used acetic anhydride/pyridine/DCM (1:8:8) for 20 minutes to avoid any deletion of the sequence. After capping, resin was washed with DCM (6×10 mL), DMF (6×10 mL), DCM (6×10 mL) and DMF (6×10 mL). The Fmoc group on the C-terminal amino acid attached peptidyl resin was deprotected by treating it twice with 20% (v/v) piperdine/DMF solution for 5 and 15 min (10 mL). The resin was washed with DMF (6×10 mL), DCM (6×10 mL) and DMF (6×10 m L). Kaiser test on peptide resin aliquot upon completion of Fmoc-deprotection was positive. Fmoc-Ser (OtBu)-OH (0.9 g; 5 equiv. 2.3 m mol) in dry DMF was added to the deprotected resin and coupling was initiated with DIC (0.36 mL; 5 equiv) and HOBT (0.32 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The Fmoc group of the peptidyl resin was deprotected by treating it twice with 20% (v/v) piperdine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. Next amino acid in the peptide sequence Fmoc-Thr (OtBu)-OH (0.92 g; 5 equiv. 2.3 m mol) in dry DMF was added to the deprotected resin and coupling was initiated with DIC (0.36 mL; 5 equiv) and HOBT (0.32 g; 5 equiv) in DMF. The concentration of each reactant in the reaction mixture was approximately 0.4 M. The mixture was rotated on a rotor at room temperature for 2 h. Resin was filtered and washed with DMF (6×10 m L), DCM (6×10 mL) and DMF (6×10 mL). Kaiser test on peptide resin aliquot upon completion of coupling was negative. On completion of threonine coupling Fmoc group on the threo- (SEQ ID NO: 3)

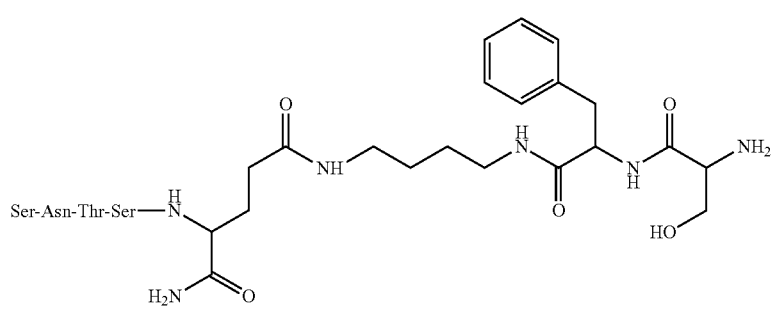

Resin: 1 g CLEAR Amide Resin (RCY 1250-PI, Lot No. 224481), 0.46 mmol/g

Desiccated CLEAR Amide resin (0.46 mmol/g, 1 g) was placed in a polyethylene vessel equipped with a polypropylene filter. Resin was swelled in DCM (15 mL) for 1 h and DMF (15 mL) for 1 h. The Fmoc group of the CLEAR Amide was deprotected by treating it twice with 20% (v/v) piperdine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. The C-terminal amino acid, Fmoc-Glu(OAllyl)-OH (0.98 g; 5 equiv. 2.3 mmol) in dry DMF was added to the deprotected resin and nine was deprotected by treating it twice with 20% (v/v) piperdine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. Next amino acid Fmoc-Asn (Trt)-OH (1.4 g; 5 equiv. 2.3 mmol) in dry DMF was added to the deprotected resin and coupling was initiated with DIC (0.36 mL; 5 equiv) and HOBT (0.32 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The Fmoc group on the peptidyl resin was deprotected by treating it twice with 20% (v/v) piperdine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. Boc-Ser (OtBu)-OH (0.62 g; 5 equiv. 2.3 m mol) in Dry DMF was added to the deprotected resin and coupling was initiated with DIC (0.36 mL; 5 equiv) and HOBT (0.32 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative. The linear chain of the sequence is completed and further chain elongation is achieved by removing the orthogonal ally ester protecting group on the Glutamic acid.

Removal of Allyl Ester (OAll) Protecting Group on the Side Chain Carboxyl Acid of Glutamic Acid After the completion of the linear protected peptide sequence, the Allyl protecting group from the carboxyl moiety of Glu was removed from the peptidyl resin by treating with tetrakistriphenylphosphine palladium (0) (10 Equiv; 5.3 g) and Phenylsilane (20 eqv; 1.2 m L) in a solution of chloroform/N-methylpyrrolidine (95/5 v/v) for 4 h under argon. The resin was washed with a solution of 10% NMP in chloroform (6×10 mL), 1% DIEPA in DMF (6×10 mL), DCM (6×10 mL), DMF (6×10 mL).

Attachment of Linker Fmoc-1,4-Diamino Butane Hydrochloride to the Carboxyl End of Glutamic Acid Fmoc 1,4-diamino butane HCL (0.24 g; 1.5 equiv. 0.69 mmol) in Dry DMF was added to the deprotected resin and coupling was initiated with DIC (0.18 mL; 1.2 m mol equiv) and HOBT (0.08 g; 0.69 m mol) in DMF. The concentration of each reactant in the reaction mixture was approximately 0.4 M. The mixture was rotated on a rotor at room temperature for overnight. Resin was filtered and washed with DMF (6×10 mL), DCM (6×15 mL) and DMF (6×10 mL). The Fmoc group of the linker attached to peptidyl resin was deprotected by treating it twice with 20% (v/v) piperdine/DMF solution for 5 and 15 min (10 mL). The resin was washed with DMF (6×10 mL), DCM (6×10 m L) and DMF (6×10 mL). Kaiser test on peptide resin aliquot upon completion of Fmoc-deprotection was positive. Next amino acid Fmoc-Phe-OH (0.89 g; 5 equiv. 2.3 mmol) in dry DMF was added to the deprotected resin and coupling was initiated with DIC (0.43 mL; 6 equiv) and HOBT (0.32 g; 5 equiv) in DMF. The concentration of each reactant in the reaction mixture was approximately 0.4 M. The mixture was rotated on a rotor at room temperature for 2 h. Resin was filtered and washed with DMF (6×10 m L), DCM (6×10 mL) and DMF (6×10 mL). Kaiser test on peptide resin aliquot upon completion of coupling was negative. The Fmoc group of the peptidyl resin was deprotected by treating it twice with 20% (v/v) piperdine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. The last amino acid of the complete sequence Boc-Ser (OtBu)-OH (0.62 g; 5 equiv. 2.3 mmol) in dry DMF was added to the deprotected resin and coupling was initiated with DIC (0.43 mL; 6 equiv) and HOBT (0.32 g; 5 equiv) in DMF. The concentration of each reactant in the reaction mixture was approximately 0.4 M. The mixture was rotated on a rotor at room temperature for 2 h. Resin was filtered and washed with DMF DMF (6×10 mL), DCM (6×10 mL) and DMF (6×10 mL). Kaiser test on peptide resin aliquot upon completion of coupling was negative.

Final Cleavage of Peptide from the Resin

The peptidyl resin was washed with, DCM (6×10 mL), MeOH (6×10 mL) and ether (6×10 mL) and dried in vacuum desiccators overnight. The cleavage of the peptide from the solid support was achieved by treating the peptide-resin with reagent cocktail (90.0% TFA/5% TIPS/5% $H_2O$) at room temperature for 2.5 h. Cleavage mixture was collected by filtration and the resin was washed with TFA (2 mL) and DCM (2×5 mL).

The excess TFA and DCM was concentrated to small volume under nitrogen and a small amount of DCM (5-10 mL) was added to the residue and evaporated under nitrogen. The process was repeated 3-4 times to remove most of the volatile impurities. The residue was cooled to 0° C. and anhydrous ether was added to precipitate the peptide. The precipitated peptide was centrifuged and the supernatant ether was removed and fresh ether was added to the peptide and re-centrifuged (270 mg, 70% yield). The residue was dissolved in Millipore water and lyophilized to obtain the crude peptide. The crude sample was preparative HPLC purified on Zorbax Eclipse XDB-C18 column (9.4 mm×250 mm, 5 μm) with buffer A: 0.1% TFA/Water, buffer B: Acetonitrile. The peptide was eluted by gradient elution 0-5 min=5% buffer B, 5-25 min=5-60% buffer B with a flow rate of 7 mL/min. The identity of peptide was confirmed by LCMS. Calculated Mass: 840, Observed Mass: 840.4[M]$^+$.

Example 2

Synthesis of Compound 2

(SEQ ID NO: 4)

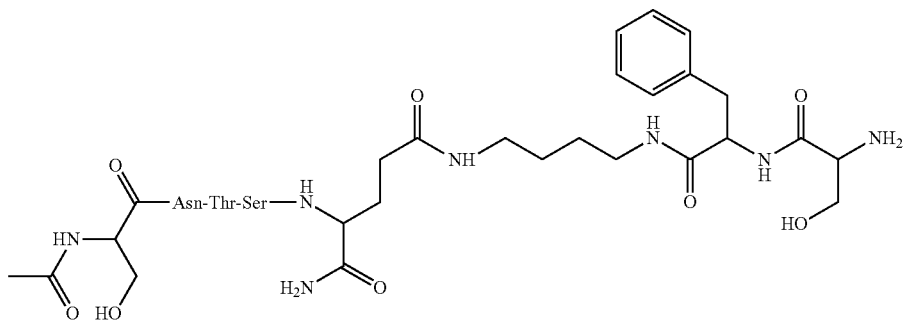

The synthesis was carried out manually using the same method as in example 1 using desiccated Rink Amide MBHA-Amide resin (100-200 mesh, 0.66 mmol/g, 0.75 g). The N-terminal amino acid serine was coupled as Fmoc-Ser-(OtBu)-OH as detailed in example 1. The Fmoc group of the linker attached to peptidyl resin was deprotected by treating it twice with 20% (v/v) piperdine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deprotection was positive. The free amine was acetylated using acetic anhydride/pyridine/DCM (1:8:8) for 20 minutes. After acetylation, resin is washed with DCM (6×10 mL); DMF (6×10 mL), DCM (6×10 mL), and DMF (6×10 mL). Kaiser test on peptide resin aliquot upon completion of coupling was negative. The linear chain of the sequence is completed and further chain elongation is achieved by removing the orthogonal allyl ester protecting group on the Glutamic acid as mentioned in example 1 to yield 300 mg, 70% crude peptide (300 mg, 70% yield). The crude sample was preparative HPLC purified on Zorbax Eclipse XDB-C18 column (9.4 mm×250 mm, 5 μm) with buffer A: 0.1% TFA/Water, buffer B: Acetonitrile. The peptide was eluted by gradient elution 0-8 min=5-15% buffer B, 8-10 min=15-20% buffer B with a flow rate of 7 mL/min The identity of peptide was confirmed by LCMS. Calculated Mass: 882.3, Observed Mass: 882.6 [M]+.

pound as white solid [yield: 3.1 g, 88.6%; ELSD-HPLC: 99%, Mass: Cal. 259.18, Obs—260.2]

Acid-amine hydrochloride A (2.5 g, 8.4 mmol) was dissolved in DCM (25 mL) together with catalytic amount of hydroquinone (10 mg), and poured in to a solution of di-tert-butyl dicarbonate (1.84 g, 8.4 mmol) and triethyl amine (3.5 mL, 25.4 mmol) in DCM (20 mL). The solution was then refluxed for 30 min to give a clear solution and cooled in an ice bath. A solution of NaHSO$_4$ (4 g in 40 mL water) was added, the reaction mixture was then partitioned between water and DCM, and the aqueous phase was extracted once again with DCM (25 mL). The combined organic phases were washed with brine, dried over Na$_2$SO$_4$ and evaporated in vacuo to give desired compound as colourless oil. (Yield: 3.0 g, 98.0%; ELSD-HPLC: 99%, Mass: Cal. 359.2, Obs—382 (M+Na)].

Example 3

Synthesis of Compound 4

(SEQ ID NO: 6)

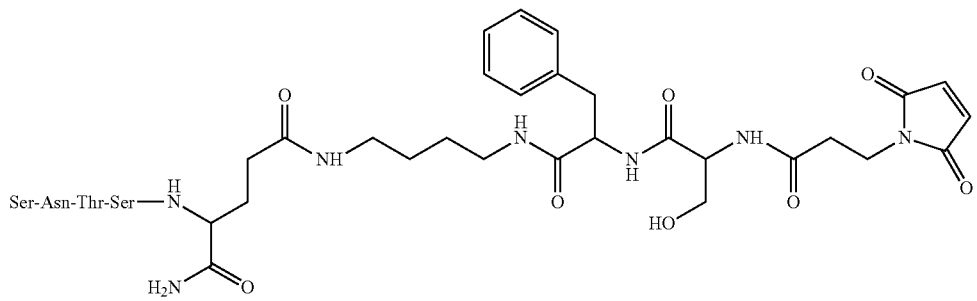

Synthesis of Building Block

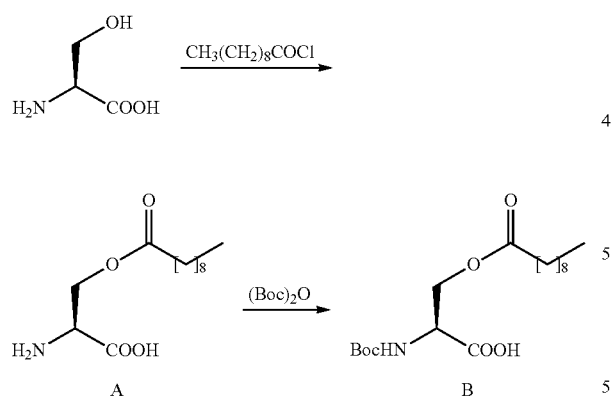

To a solution of L-Serine (1.25 g, 11.8 mmol) in 8.5 mL of TFA, Hydroquonone (catalytic-100 mg) was added at 0° C. The resulting mixture was stirred at room temperature for 10 min, to this solution at room temperature decanoyl chloride (3.4 g, 17.8 mmol) was added slowly and the reaction was allowed to continue for 2 h. After the completion of 2 h, the reaction mixture was diluted with diethylether (100 mL) and triturated at 0-50° C. to get white precipitate, which was centrifuged and dried under vacuum to furnish desired com- The synthesis was carried out as explained in example 1 using Rink Amide MBHA Resin (RFR-1063-PI Lot No 2401691), 0.66 mmol/g, 0.75 g. After the completion of linear synthesis, orthogonal deprotection, coupling of phenyl alanine and serine was carried out as in example 1. The N-terminus serine in the branch was coupled as Fmoc-Ser(OtBu)-OH and on completion of serine coupling as evidenced by Kaiser test, Fmoc-deprotection was carried out. The next residue 3-malemidopropanoic acid (0.17 g; 2 equiv. 0.99 mmol) in dry DMF was added to the deprotected resin and coupling was initiated with DIC (0.23 mL; 3 equiv) and HOBT (0.13 g; 2 equiv) in DMF. The concentration of each reactant in the reaction mixture was approximately 0.4 M. The mixture was rotated on a rotor at room temperature for overnight. Resin was filtered and washed with DMF DMF (6×10 mL), DCM (6×10 mL) and DMF (6×10 mL). Kaiser test on peptide resin aliquot upon completion of coupling was negative. The final cleavage of peptidyl resin was carried out as in example 1 to yield 300 mg, 70% yield of crude peptide. The crude sample was preparative HPLC purified on Zorbax Eclipse XDB-C18 column (9.4 mm×250 mm, 5 μm) with buffer A: 0.1% TFA/Water, buffer B: Acetonitrile. The peptide was eluted by gradient elution 0-5 min=5-10% buffer B, 5-9 min=10-25% buffer B with a flow rate of 7 mL/min. The identity of peptide was confirmed by LCMS. Calculated Mass: 990.3, Observed Mass: 991.4[M+H]+.

Example 4

Synthesis of Compound 16

(SEQ ID NO: 18)

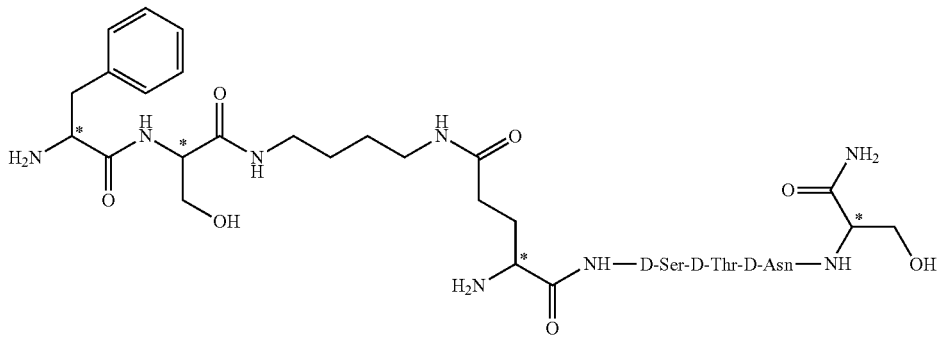

The synthesis was carried out as explained in example 1 using Rink Amide MBHA Resin (RFR-1063-PI Lot No 2401691), 0.66 mmol/g, and 0.75 g. In this example Fmoc-D-Ser(OtBu) was coupled as the C-terminal amino acid. The synthesis was continued using D-amino acids. D-Boc-Glu(OAllyl)-OH was used as the building block to incorporate Glutamic acid. Coupling of amino acids and cleavage of peptidyl resin was carried out as mentioned in example 1 to yield 300 mg, 70% yield of crude peptide The crude sample was preparative HPLC purified on Zorbax Eclipse XDB-C18 column (9.4 mm×250 mm, 5 μm) with buffer A: 0.1% TFA/Water, buffer B: Acetonitrile. The peptide was eluted by gradient elution 0-9 min=5-20% buffer B, with a flow rate of 7 mL/min. The identity of peptide was confirmed by LCMS. Calculated Mass: 840, Observed Mass: 841[M+H]$^+$.

Synthesis of Building Block

Compound E (1.0 g, 1.44 mmol) was dissolved in 20 mL of DCM containing triethyl amine (0.218 g, 2.16 mmol) at −20° C. At same temperature, isobutyl chloroformate (0.216 g, 1.5 mmol) was added slowly, and the mixture was stirred for 1 h at −20° C. under $N_2$ atmosphere. A further quantity of isobutyl chloroformate (0.216 g, 1.5 mmol) and triethyl amine (0.218 g, 2.16 mmol) was added and stirring was continued at 0° C. until the reactants were consumed as determined by TLC analysis. The reaction mixture concentrated under reduced pressure and diluted with EtOAc, the organic extract was washed with water (50 mL×2), brine (50 mL) and dried ($Na_2SO_4$). The solvent was evaporated to give the crude product which was further purified by silica gel column chromatography (eluent: 0-40% EtOAc in Hexane) to furnish the product I (yield: 0.92 g,: 80.7%; Mass: Cal. 793.43, Obs—794.3 (M+1), 817.3 (M+Na).

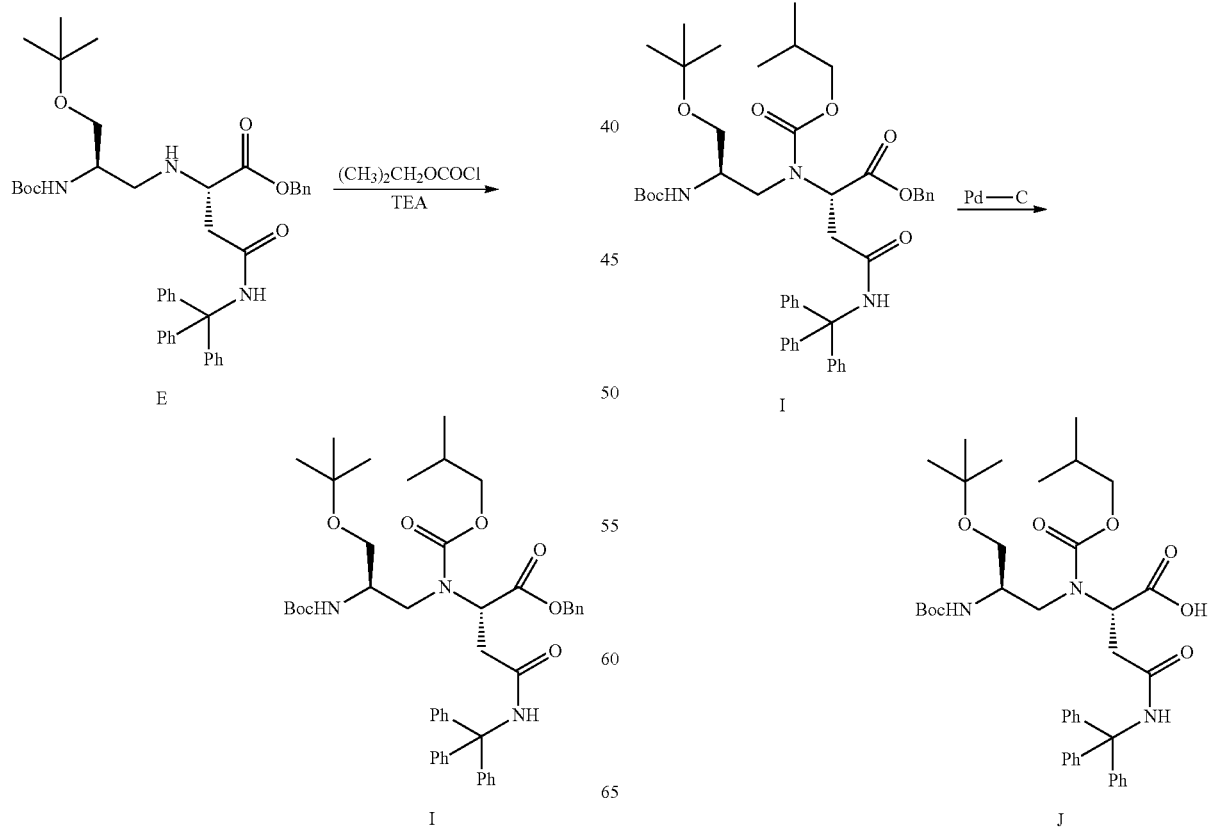

To a solution of compound I (0.68 g) in methanol (10 mL) under inert atmosphere was added 10% Pd—C (0.25 g), and the mixture was stirred for 4 h under H, atmosphere. The completion of the reaction was confirmed by TLC analysis. After the completion of reaction, the catalyst was removed by filtration through a celite pad, which was then washed with 30 mL of methanol. The combined organic filtrate, on evaporation under reduced pressure resulted in the isolation of pure product J (yield: 0.58 g, 96%, Mass: Cal. 703.38, Obs—704.3 (M+1), 726.3 (M+Na).

Example 5

Synthesis of Compound 18

(SEQ ID NO: 20)

The synthesis was carried out as explained in example 1 using Rink Amide MBHA Resin (RFR-1063-PI Lot No 2401691), 0.66 mmol/g, 0.75 g. The N-terminal amino acid in the linear chain was coupled as Boc-Ser-(OCO(CH$_2$)$_8$CH$_3$)—OH (compound B, 0.27 g; 1.5 equiv. 0.745 mmol) in dry DMF was added to the deprotected resin and coupling was initiated with DIC (0.2 mL; 2.5 equiv) and HOBT (0.1 g; 1.5 equiv) in DMF. The concentration of each reactant in the reaction mixture was approximately 0.4 M. The mixture was rotated on a rotor at room temperature for overnight. Resin was filtered and washed with DMF (6×10 mL), DCM (6×10 mL) and DMF (6×10 mL). After the completion of the linear protected peptide sequence, the Allyl protecting group from carboxyl moiety of Glutamic acid was removed from the peptidyl resin and synthesis continued in the branch as mentioned in example 1 to yield 363 mg, 75% yield of crude peptide. The crude sample was preparative HPLC purified on Zorbax Eclipse XDB-C18 column (9.4 mm×250 mm, 5 µm) with buffer A: 0.1% TFA/Water, buffer B: Acetonitrile. The peptide was eluted by gradient elution 0-5 min=5-15% buffer B, 5-10 min=15-25% buffer B with a flow rate of 7 mL/min. The identity of peptide was confirmed by LCMS. Calculated Mass: 980, observed mass 980.4 [M]$^+$ Synthesis of Building Block To a solution of N-Boc amino acid (10.0 g, 38.28 mmol) in THF (100 mL) at −20° C., was added N-methyl morpholine (NMM, 4.25 g, 42.11 mmol) and ethylchloroformate (4.57 g, 42.11 mmol) and the resultant mixture was stirred at same temperature for 20 min. The inorganic salts were filtered off and the filtrate was treated with moist NaBH$_4$ (2.9 g, 76.56 mmol) for 10-15 min. The reaction mixture was then partitioned between water and EtOAc. Organic layer was washed with water, 10% NaHCO$_3$ solution (100 mL x 2) and brine, dried over Na$_2$SO$_4$ and evaporated under reduced pressure to yield N-Boc aminol, which was further purified by silica gel column chromatography (eluent: 0-50% EtOAc in Hexane) to yield 8.2 g of product [yield: 85.4%, Mass: Cal. 247.3, Obs: 248.2 (M+1), 270.2 (M+Na)].

To the solution of N-Boc-aminol (3.0 g, 12.13 mmol) in distilled DCM (30.0 mL) was added Dess-Martin periodinane (10.3 g, 24.27 mmol) in a portion wise manner at 0° C. and stirred at rt under $N_2$ atmosphere for 30 min until the reactants were consumed as determined by TLC analysis. The reaction mixture was quenched by adding 1.0M $Na_2S_2O_3$ solution, and the product was extracted with DCM. The organic extract was washed with (5%, 1:1) $Na_2S_2O_3$/ $NaHCO_3$ solution (20 mL x 2), brine (20 mL) and dried over $Na_2SO_4$. The solvent was removed under reduced pressure to give the crude product, which was further purified by silica gel column chromatography (eluent: 0-20% EtOAc in Hexane) to yield 2.4 g pure product C (yield-82%, Mass-Cal. 245.32, Obs—247.9 (M+1), 265.1 (M+Na)).

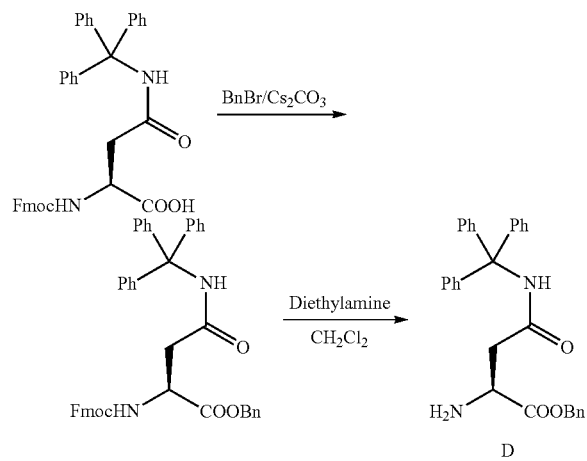

To a solution of Fmoc-Asn(trt)-OH (4.0 g, 6.7 mmol) in 30.0 mL of DMF was added $Cs_2CO_3$ (2.62 g, 8.0 mmol). The mixture was then cooled to 0° C. and benzyl bromide (1.37 g, 8.0 mmol) was added and the resultant solution was stirred for 30 min at 0° C. and then at rt for 12 h. The reaction mixture was concentrated under reduced pressure and diluted with EtOAc (50 mL), the organic layer was washed with $NaHCO_3$ (2×50 m L) and brine (1×50 mL), dried over $Na_2SO_4$, filtered and concentrated in vacuo and purified by silica gel column chromatography (eluent: 0-30% EtOAc in Hexane) to furnish Fmoc-Asn(trt)-OBn as white solid [yield: 4.5 g, 98.0%; Mass: Cal. 686.28, Obs—687.3 (M+1), 709.1 (M+Na].

To a solution of Fmoc-Asn(Trt)-OBn (3.5 g, 5.1 mmol) in DCM (14.0 mL), diethylamine (14.0 mL) was added and stirred for 1 h at rt. The resulting solution was concentrated in vacuo and the thick-residue was purified by neutral alumina column chromatography (eluent: 0-50% EtOAc in Hexane then 0-5% MeOH in $CHCl_3$) to yield $NH_2$-Asn(Trt)-OBn D (yield: 1.75 g, 73.0%; Mass: Cal. 464.21, Obs—465.3 (M+1), 487.2 (M+Na]).

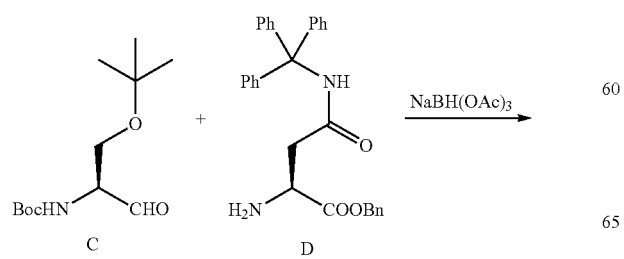

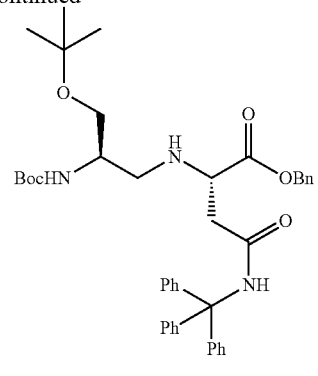

Asn(Trt)-OBn (4.5 g, 9.7 mmol), DIPEA (2.5 g, 19.4 mmol) and Boc-Ser(OtBu)-CHO (2.4 g, 9.7 mmol) were mixed in DCM (45 mL) at 0° C. and then allowed to stir at room temperature for 1 h. Again the reaction mixture was cooled to 0° C. and treated with sodium triacetoxyborohydride (4.1 g, 19.4 mmol) and then mixture was allowed to stir at room temperature under $N_2$ atmosphere for 6 h until the reactants were consumed as determined by TLC analysis. The reaction mixture was quenched by adding water, and the product was extracted with DCM. The organic extract was washed with 5% $NaHCO_3$ solution (50 mL×2), 5% citric acid solution (50 mL×2), brine (50 mL) and dried over $Na_2SO_4$. The solvent was evaporated to give the crude product which was further purified by silica gel column chromatography (eluent: 5-40% EtOAc in Hexane) to furnish the desired product E (yield: 4.2 g, 62.0%; Mass: Cal. 693.27, Obs—694.4 (M+1), 716.0 (M+Na)).

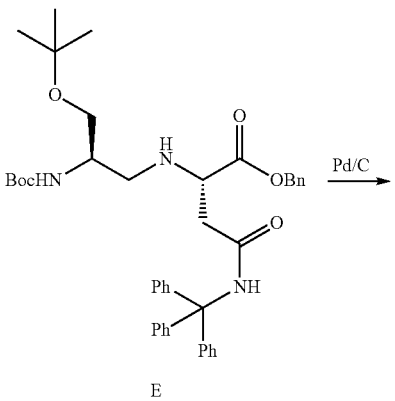

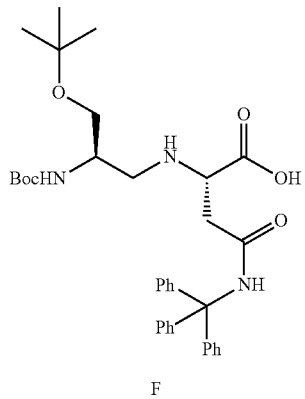

To a solution of compound E (4.0 g) in methanol (70.0 mL) under inert atmosphere, was added 10% Pd—C (1.0 g) and the mixture was stirred for 4 h under $H_2$ atmosphere. The completion of the reaction was confirmed by TLC analysis. The catalyst was then removed by filtration through a celite pad, which was then washed with 50 mL of methanol. The combined organic filtrate, on evaporation under reduced pressure resulted in the isolation of the product F, (Yield: 3.3 g, 96.0%; Mass: Cal. 603.25, Obs—604.4 (M+1), 626.4 (M+Na).

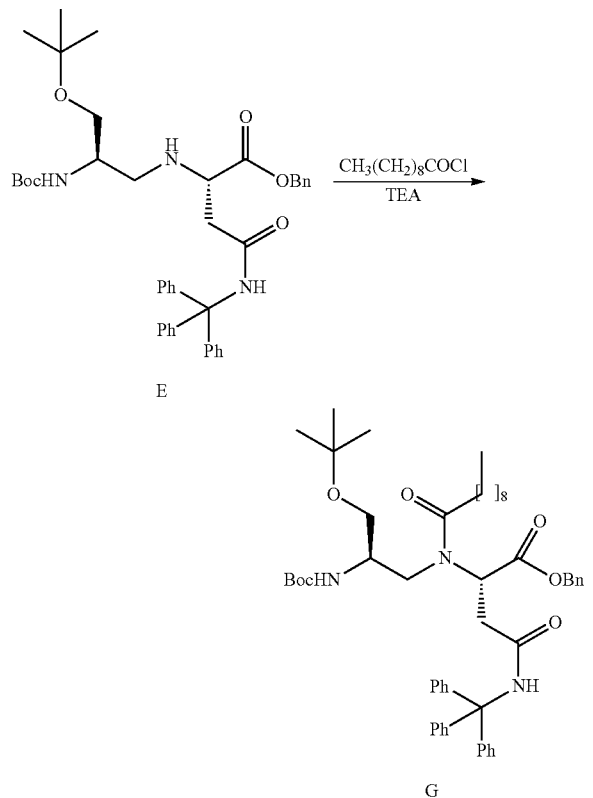

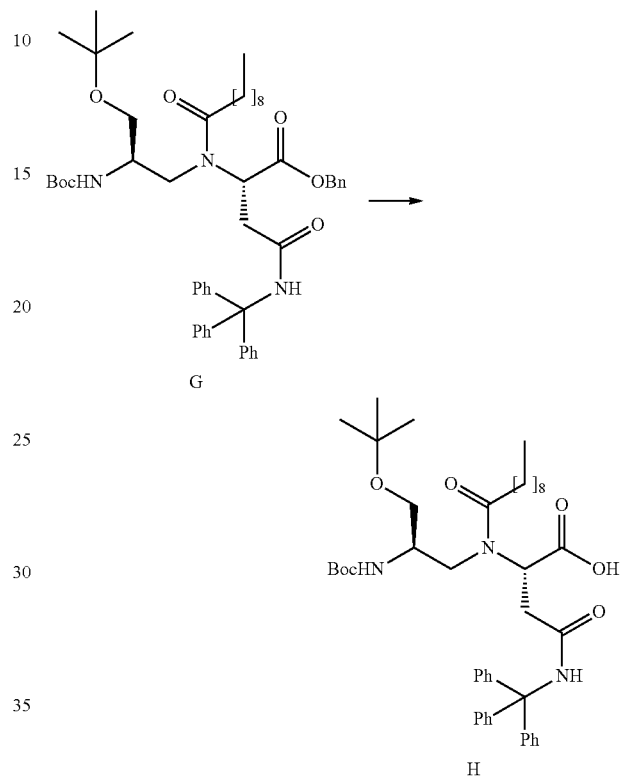

Compound E (0.96 g, 1.38 mmol) was dissolved in 20 mL of DCM containing triethyl amine (0.384 g, 2.7 mmol) at 0° C. At same temperature, decanoyl chloride (0.263 g, 1.38 mmol) was added slowly, and the mixture was stirred for 5 min at 0° C., and at rt for 1 h under $N_2$ atmosphere. A further quantity of decanoyl chloride (0.263 g, 1.38 mmol) and triethyl amine (0.384 g, 2.7 mmol) was added and stirring was continued until the reactants were consumed as determined by TLC analysis. The reaction mixture was quenched by adding water, and the product was extracted with DCM. The organic extract was washed with water (50 mL×2), brine (50 mL) and dried ($Na_2SO_4$). The solvent was evaporated to give the crude product which was further purified by silica gel column chromatography (eluent: 0-40% EtOAc in Hexane) to furnish the product G (yield: 0.87 g, 81.9%; Mass: Cal. 847.2, Obs—848.3 (M+1), 870.4 (M+Na).

To a solution of compound G (0.72 g, 0.85 mmol) in methanol (10 mL) under inert atmosphere was added 10% Pd—C (0.25 g), and the mixture was stirred for 4 h under $H_2$ atmosphere. The completion of the reaction was confirmed by TLC analysis. After the completion of reaction, the catalyst was removed by filtration through a celite pad, which was then washed with 30 mL of methanol. The combined organic filtrate, on evaporation under reduced pressure resulted in the isolation of pure product H (yield: 0.58 g, 90.6%, Mass: Cal. 757.3, Obs—758.2 (M+1), 780.3 (M+Na).

Example 6

Synthesis of Compound 20

(SEQ ID NO: 22)

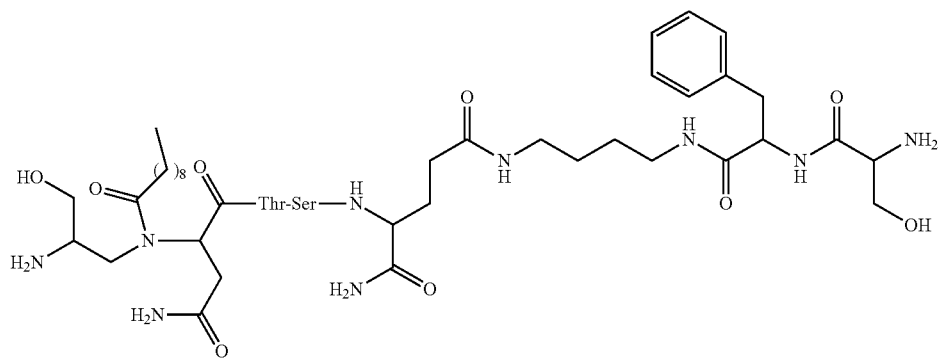

The synthesis was carried out as explained in example 1 using Rink Amide MBHA Resin (RFR-1063-PI Lot No 2401691), 0.66 mmol/g, 0.75 g. The N-terminal amino acid in the linear chain was coupled as (compound H, 0.56 g; 1.5 equiv. 0.74 m mol) in Dry DMF was added to the deprotected resin and coupling was initiated with DIC (0.2 mL; 2.5 equiv) and HOBT (0.1 g; 1.5 equiv) in DMF. The concentration of each reactant in the reaction mixture was approximately 0.4 M. The mixture was rotated on a rotor at room temperature for overnight. Resin was filtered and washed with DMF (6×10 mL), DCM (6×10 mL) and DMF (6×10 mL). After the completion of the linear protected peptide sequence, the orthogonal deprotection, attachment of linker and coupling of phenyl alanine and serine was carried out as in example 1. The peptide was cleaved from the polymeric support to yield 300 mg, 66% yield of crude peptide. The crude sample was preparative HPLC purified on Zorbax Eclipse XDB-C18 column (9.4 mm×250 mm, 5 μm) with buffer A: 0.1% TFA/Water, buffer B: Acetonitrile. The peptide was eluted by gradient elution 0-5 min=5-15% buffer B, 5-10 min=15-25% buffer B with a flow rate of 7 mL/min. The identity of peptide was confirmed by LCMS. Calculated Mass: 925.5 Observed Mass: 926.7 [M+H]$^+$ Example 7

Synthesis of Compound 26

(SEQ ID NO: 28)

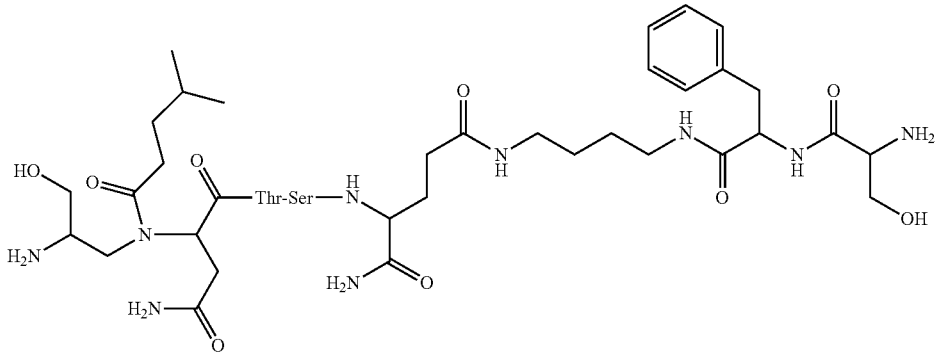

The synthesis was carried out as explained in example 1 using Rink Amide MBHA Resin (RFR-1063-PI Lot No 2401691), 0.66 mmol/g, and 0.75 g. The N-terminal amino acid in the linear fragment was coupled as (compound J, 0.52 g; 1.5 equiv. 0.745 mmol) in dry DMF was added to the deprotected resin and coupling was initiated with DIC (0.2 m L; 2.5 equiv) and HOBT (0.1 g; 1.5 equiv) in DMF. The concentration of each reactant in the reaction mixture was approximately 0.4 M. The mixture was rotated on a rotor at room temperature for overnight. Resin was filtered and washed with DMF (6×10 mL), DCM (6×10 mL) and DMF (6×10 mL). The synthesis was continued further after OAR deprotection and coupling of branch amino acids as explained in the example 1 to yield 363 mg, 75% yield of crude peptide. The crude sample was preparative HPLC purified on Zorbax Eclipse XDB-C18 column (9.4 mm×250 mm, 5 μm) with buffer A: 0.1% TFA/Water, buffer B: Acetonitrile. The peptide was eluted by gradient elution 0-5 min=5-10% buffer B, 5-20 min=10-25% buffer B with a flow rate of 7 mL/min. The identity of peptide was confirmed by LCMS. Calculated Mass: 925.5, observed mass 926.7 [M+H]$^+$.

Example 8

Synthesis of Compound 28

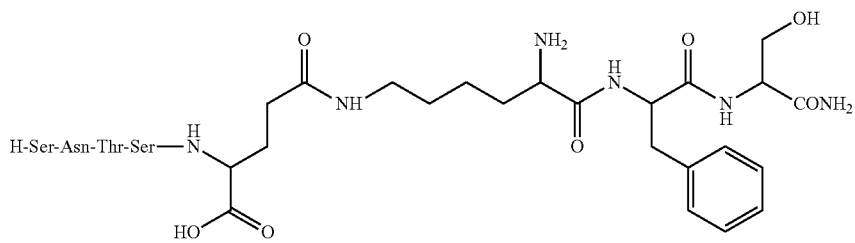

Desiccated Rink Amide MBHA-Amide resin (100-200 mesh, 0.66 mmol/g, 0.5 g) was placed in a polyethylene vessel equipped with a polypropylene filter. Resin was swelled in DCM (15 mL) for 1 h and DMF (15 mL) for 1 h. The Fmoc group of the Rink Amide MBHA-Amide was deprotected by treating it twice with 20% (v/v) piperidine/DMF solution for 5 and 15 min (10 mL). The resin was washed with DMF (6×10 mL), DCM (6×10 mL) and DMF (6×10 mL). Kaiser test on peptide resin aliquot upon completion of Fmoc-deportation was positive. The C-terminal amino acid, Fmoc-Ser(tBu)-OH (0.64 g; 5 equiv. 1.65 mmol) in dry DMF was added to the deprotected resin and coupling was initiated with DIC (0.26 mL; 5 equiv) and HOBT (0.23 g; 5 equiv) in DMF. The concentration of each reactant in the reaction mixture was approximately 0.4 M. The mixture was rotated on a rotor at room temperature for 2 h. Resin was filtered and washed with DMF (6×10 mL), DCM (6×10 mL) and DMF (6×10 mL). Kaiser test on peptide resin aliquot upon completion of coupling was negative After the first amino acid attachment, the unreacted amino group, if any, in the resin is capped used acetic anhydride/pyridine/DCM (1:8:8) for 20 minutes to avoid any deletion of the sequence. After capping, resin is washed with DCM (6×10 mL), DMF (6×10 mL), DCM (6×15 mL) and DMF (6×15 mL). The Fmoc group on the C-terminal amino acid attached peptidyl resin was deprotected by treating it twice with 20% (v/v) piperdine/DMF solution for 5 and 15 min (15 mL). The resin was washed with DMF (6×10 mL), DCM (6×10 mL) and DMF (6×10 mL). Kaiser test on peptide resin aliquot upon completion of Fmoc-deprotection was positive. The remaining amino acids were attached to the solid support as mentioned in example 1. The following amino acids were added sequentially to the peptidyl resin; Fmoc-Phe-OH (0.64 g; 5 equiv. 1.65 mmol), Boc-Lys(Fmoc)-OH (0.78 g; 5 equiv. 1.65 mmol), Fmoc-Glu(OtBu)-OH (0.7 g; 5 equiv. 1.65 mmol), Fmoc-Ser(tBu)-OH (0.64 g; 5 equiv. 1.65 mmol), Fmoc-Thr(OtBu)-OH (0.66 g; 5 equiv. 1.65 mmol), Fmoc-Asn(Trt)-OH (0.98 g; 5 equiv. 1.65 mmol), Fmoc-Ser (OtBu)-OH (0.64 g; 5 equiv. 1.65 mmol). The coupling was carried out in dry DMF using DIC (0.26 mL; 5 equiv) and HOBT (0.23 g; 5 equiv) in DMF. The cleavage of the peptidyl resin was carried out as mentioned in example 1. The precipitated peptide was centrifuged and the supernatant ether was removed and fresh ether was added to the peptide and re-centrifuged. The residue was dissolved in Millipore water and lyophilized to obtain the crude peptide (222 mg, 75% yield). The crude sample was preparative HPLC purified and Lyophilised. The identity of peptide was confirmed by LCMS. Calculated Mass: 897.4, Observed Mass: 898.4 [M+1]$^+$.

The following compounds were prepared by following similar procedure as described above with similar modification known to the one ordinary skilled in the art. The identity of peptide was confirmed by LCMS (Table 2).

TABLE 2

| Comp | LCMS | |
|---|---|---|
| No. | Calculated | Observed |
| 001 | 840 | 840.6 [M]$^+$ |
| 002 | 882.3 | 882.6 [M]$^+$ |
| 003 | 1077.2 | 1078.8 [M + H]$^+$ |
| 004 | 990.3 | 991.4 [M + H]$^+$ |
| 005 | 1135.1 | 1136.1 [M + H]$^+$ |
| 006 | 840 | 841 [M + H]$^+$ |
| 007 | 868.6 | 869.6 [M + H]$^+$ |
| 008 | 840 | 840.4 [M]$^+$ |

TABLE 2-continued

| Comp | LCMS | |
|---|---|---|
| No. | Calculated | Observed |
| 009 | 840 | 840.5 [M]$^+$ |
| 010 | 896.1 | 897.1 [M + H]$^+$ |
| 011 | 840 | 840.4 [M]$^+$ |
| 012 | 840 | 840.5 [M]$^+$ |
| 014 | 896.1 | 897.1 [M + H]$^+$ |
| 015 | 840 | 841 [M + H]$^+$ |
| 016 | 840 | 841 [M + H]$^+$ |
| 017 | 840 | 840.4 [M]$^+$ |
| 018 | 993.5 | 994.5 [M + H]$^+$ |
| 019 | 826.1 | 827.1 [M + H]$^+$ |
| 020 | 980 | 980.4 [M]$^+$ |
| 025 | 925.5 | 926.7 [M + H]$^+$ |
| 026 | 925.5 | 926.7 [M + H]$^+$ |
| 028 | 897.42 | 898.4 [M + H]$^+$ |
| 029 | 810.39 | 811.3 [M + H]$^+$ |
| 030 | 696.34 | 697.7 [M + H]$^+$ |
| 031 | 595.30 | 596.4 [M + H]$^+$ |

The remaining compounds of the Table 1 can be prepared by following similar approach as described above.

Use of MDA-MB-231 Cells as a Source of PD-L1:

MDA-MB-231 cells were found to express PD-L1 by RT-PCR and therefore used as a source of PD-L1 in the assays.

Example 9

The Effect of Peptides on Mouse Splenocyte Proliferation Inhibited by PDL1/PDL2 or Tumor Cells Expressing PDL Requirement:

Mouse splenocytes harvested from 6-8 weeks old C57 BL6 mice; RPMI 1640 (GIBCO, Cat #11875); DMEM with high glucose (GIBCO, Cat # D6429); Fetal Bovine Serum [Hyclone, Cat # SH30071.03]; Pencilin (10000 unit/ml)-Streptomycin (10,000 µg/ml) Liquid (GIBCO, Cat #15140-122); MEM Sodium Pyruvate solution 100 mM (100×), Liquid (GIBCO, Cat #11360); Nonessential amino acid (GIBCO, Cat #11140); L-Glutamine (GIBCO, Cat #25030); Anti-CD3 antibody (eBiosciences—16-0032); Anti-CD28 antibody (eBiosciences—16-0281); ACK lysis buffer (1 mL) (GIBCO, Cat #—A10492); Histopaque (density-1.083 gm/ml) (SIGMA 10831); Trypan blue solution (SIGMA-T8154); Hemacytometer (Bright line-SIGMA Z359629); FACS Buffer (PBS/0.1% BSA): Phosphate Buffered Saline (PBS) pH 7.2 (HiMedia TS1006) with 0.1% Bovine Serum Albumin (BSA) (SIGMA A7050) and sodium azide (SIGMA 08591); 5 mM stock solution of CFSE:CFSE stock solution was prepared by diluting lyophilized CFSE with 180µL of Di methyl Sulfoxide (DMSO C$_2$H$_6$SO, SIGMA-D-5879) and aliquoted in to tubes for further use. Working concentrations were titrated from 10 µM to 1 µM. (eBioscience-650850-85); 96-well format ELISA plates (Corning CLS3390); BD FACS caliber (E6016).

Protocol

Splenocyte Preparation:

Splenocytes harvested in a 50 ml falcon tube by mashing spleen in a 40 µm cell strainer were further treated with 1 ml ACK [Ammonium-Chloride-Potassium (K) (chloride)] lysis buffer for 5 mins at RT. After washing with 9 ml of RPMI complete media, cells re-suspended in 3 ml of 1×PBS in a 15 ml tube. 3 ml of histopaque was added very carefully to the bottom of the tube without disturbing overlaying splenocyte suspension. Spin the tube at 800×g for 20 mins at RT. Opaque layer of lymphocytes is collected carefully without disturbing/mixing any of the layers. Cells washed twice with cold 1×PBS followed by total cell counting using trypan blue exclusion method and used further for cell based assays.

CFSE Proliferation Assay:

CFSE is dye abbreviated as Carboxyfluorescein Diacetate Succinimidyl Ester that passively diffuses into cells and binds to intracellular proteins.

Tumor cells (MDMBA231) are cultured and maintained in high glucose complete DMEM media. 1×10⁵ tumor cells were plated in 96 well plates along with required conc. of PD1 derived peptide and allowed to adhere at 37° C. for 4 hrs. 1×10⁶ cells/ml of harvested splenocytes are treated with 5 μM of CFSE in pre warmed 1×PBS/0.1% BSA solution for 10 mins at 37° C. Excess CFSE was quenched using 5 volumes of ice-cold culture media to the cells and incubated on ice for 5 mins. CFSE labeled splenocytes were further given three washes with ice cold complete DMEM media. CFSE labeled 1×10⁵ splenocytes added to above wells containing tumors cells and PD1 peptides. Splenocytes were stimulated with anti-CD3 and anti-CD28 antibody (1 μl ml each) and the co-culture was further incubated for 72 hrs at 37° C. with 5% $CO_2$. Cells were harvested and washed thrice with ice cold FACS buffer and % proliferation was analyzed using a FACS caliber with 488 nm excitation and 521 nm emission filters. Each experimental condition was carried out in triplicates and each experiment at least carried out three times. % splenocyte proliferation was analyzed using cell quest FACS program and fold induction was calculated by normalizing individual values to % background proliferation (FIG. 1).

Fold Induction=% splenocyte proliferation/% background proliferation

Stimulated splenocytes: Splenocytes+anti-CD3/CD28 stimulation

Background proliferation: Splenocytes+anti-CD3/CD28+ PDL or Tumor

Peptide effect: Splenocytes+anti-CD3/CD28+PDL or Tumor+Peptide (100 nM)

Example 10

In vivo Efficacy of Compound 1 on Metastasis of B16F10 Melanoma

Animals:

C57/b16J female mice (Aurigene, Bangalore, India) aged 6 to 8 weeks were used for the experiment. Animals were acclimatized for a week in the experimental room before conducting the experiment.

Effect of Compound 001 in B16F10 Metastasis Model

In the case of metastasis model, 0.1×10⁶ B16F10 cells were injected to C57/b16J mice through i.v. Compound 001 dissolved in PBS, pH 7.4 was dosed subcutaneously at 5 mg/kg once daily. Vehicle control group of mice received only saline. Each group consisted of ten animals. Body weight and clinical signs were recorded daily. After 14 days of treatment, lung metastasis was quantitated by counting number of nodules under dissection microscope. Compound 001 treated at 5 mg/kg showed 64 percent reduction in metastasis.

SEQUENCE LISTING

```
<160> NUMBER OF SEQ ID NOS: 33

<210> SEQ ID NO 1
<211> LENGTH: 137
<212> TYPE: PRT
<213> ORGANISM: Homo sapiens
<220> FEATURE:
<221> NAME/KEY: PEPTIDE
<223> OTHER INFORMATION: Extracellular domain of Human PD1

<400> SEQUENCE: 1

Pro Pro Thr Phe Ser Pro Ala Leu Leu Val Val Thr Glu Gly Asp Asn
1               5                   10                  15

Ala Thr Phe Thr Cys Ser Phe Ser Asn Thr Ser Glu Ser Phe Val Leu
            20                  25                  30

Asn Trp Tyr Arg Met Ser Pro Ser Asn Gln Thr Asp Lys Leu Ala Ala
        35                  40                  45

Phe Pro Glu Asp Arg Ser Gln Pro Gly Gln Asp Cys Arg Phe Arg Val
    50                  55                  60

Thr Gln Leu Pro Asn Gly Arg Asp Phe His Met Ser Val Val Arg Ala
65                  70                  75                  80

Arg Arg Asn Asp Ser Gly Thr Tyr Leu Cys Gly Ala Ile Ser Leu Ala
                85                  90                  95

Pro Lys Ala Gln Ile Lys Glu Ser Leu Arg Ala Glu Leu Arg Val Thr
            100                 105                 110

Glu Arg Arg Ala Glu Val Pro Thr Ala His Pro Ser Pro Ser Pro Arg
        115                 120                 125

Ser Ala Gly Gln Phe Gln Thr Leu Val
    130                 135
```

```
<210> SEQ ID NO 2
<211> LENGTH: 7
<212> TYPE: PRT
<213> ORGANISM: Homo sapiens
<220> FEATURE:
<221> NAME/KEY: PEPTIDE
<223> OTHER INFORMATION: BC Loop

<400> SEQUENCE: 2

Ser Asn Thr Ser Glu Phe Ser
1               5

<210> SEQ ID NO 3
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 3

Ser Asn Thr Ser Glu Phe Ser
1               5

<210> SEQ ID NO 4
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1
<223> OTHER INFORMATION: N-acetylation of Ser 1
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 4

Ser Asn Thr Ser Glu Phe Ser
1               5

<210> SEQ ID NO 5
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1
<223> OTHER INFORMATION: CH3(CH2)14CO- is attached to N-terminal of Ser
      1
<220> FEATURE:
<221> NAME/KEY: MISC_FEATURE
<222> LOCATION: 5
<223> OTHER INFORMATION: Alpha C-terminal of Glu 5 is modified with NH2
```

```
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 5

Ser Asn Thr Ser Glu Phe Ser
1               5

<210> SEQ ID NO 6
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 7
<223> OTHER INFORMATION: 3-Maleimidopropanoic acid is attached to N-
      terminal of Ser 7

<400> SEQUENCE: 6

Ser Asn Thr Ser Glu Phe Ser
1               5

<210> SEQ ID NO 7
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 7
<223> OTHER INFORMATION: (8-(3-maleimido propanamido)-3,6-dioxa octanoic
      acid is attached to N-terminal of Ser 7

<400> SEQUENCE: 7

Ser Asn Thr Ser Glu Phe Ser
1               5

<210> SEQ ID NO 8
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
```

```
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 6
<223> OTHER INFORMATION: Phe 6 is D amino acid

<400> SEQUENCE: 8

Ser Asn Thr Ser Glu Phe Ser
1               5

<210> SEQ ID NO 9
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 6
<223> OTHER INFORMATION: Fourth position of phenyl in Phe 6 is
      substituted with amino methyl group

<400> SEQUENCE: 9

Ser Asn Thr Ser Glu Phe Ser
1               5

<210> SEQ ID NO 10
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1
<223> OTHER INFORMATION: Ser 1 is D amino acid
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 10

Ser Asn Thr Ser Glu Phe Ser
1               5

<210> SEQ ID NO 11
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
```

```
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 7
<223> OTHER INFORMATION: Ser 7 is D amino acid

<400> SEQUENCE: 11

Ser Asn Thr Ser Glu Phe Ser
1               5

<210> SEQ ID NO 12
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 6
<223> OTHER INFORMATION: Fourth position of phenyl in Phe 6 is
      substituted with amino methyl group
<220> FEATURE:
<221> NAME/KEY: MISC_FEATURE
<222> LOCATION: 6
<223> OTHER INFORMATION: Phe 6 is D amino acid

<400> SEQUENCE: 12

Ser Asn Thr Ser Glu Phe Ser
1               5

<210> SEQ ID NO 13
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 2
<223> OTHER INFORMATION: Asn 2 is D amino acid
<220> FEATURE:
<221> NAME/KEY: MISC_FEATURE
<222> LOCATION: 5
<223> OTHER INFORMATION: Alpha C-terminal of Glu 5 is modified with
      NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 13

Ser Asn Thr Ser Glu Phe Ser
1               5

<210> SEQ ID NO 14
<211> LENGTH: 7
<212> TYPE: PRT
<213> ORGANISM: Artificial sequence
```

```
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Glu 2 is D amino acid
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 14

Ser Asn Thr Ser Glu Phe Ser
1               5

<210> SEQ ID NO 15
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 6
<223> OTHER INFORMATION: Fourth position of phenyl in Phe 6 is
      substituted with urea group
<220> FEATURE:
<221> NAME/KEY: MISC_FEATURE
<222> LOCATION: 6
<223> OTHER INFORMATION: Phe 6 is D amino acid

<400> SEQUENCE: 15

Ser Asn Thr Ser Glu Phe Ser
1               5

<210> SEQ ID NO 16
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 6
<223> OTHER INFORMATION: Fourth position of phenyl in Phe 6 is
      substituted with acetamide group

<400> SEQUENCE: 16

Ser Asn Thr Ser Glu Phe Ser
1               5
```

```
<210> SEQ ID NO 17
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6
<220> FEATURE:
<221> NAME/KEY: MISC_FEATURE
<222> LOCATION: 1..7
<223> OTHER INFORMATION: All amino acids are D amino acids

<400> SEQUENCE: 17

Ser Asn Thr Ser Glu Phe Ser
1               5

<210> SEQ ID NO 18
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 2..3
<223> OTHER INFORMATION: 1,4-diaminobutane linked between C-terminal
      of Ser 2 and delta C-terminal of Glu 3
<220> FEATURE:
<221> NAME/KEY: MISC_FEATURE
<222> LOCATION: 3..4
<223> OTHER INFORMATION: Alpha carboxylic acid of Glu 3 is linked to
      NH2 group of Ser 4
<220> FEATURE:
<221> NAME/KEY: MISC_FEATURE
<222> LOCATION: 7
<223> OTHER INFORMATION: C-terminal of Ser 7 is modified NH2 group
<220> FEATURE:
<221> NAME/KEY: MISC_FEATURE
<222> LOCATION: 1..7
<223> OTHER INFORMATION: All amino acids are D amino acids

<400> SEQUENCE: 18

Phe Ser Glu Ser Thr Asn Ser
1               5

<210> SEQ ID NO 19
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 2..3
<223> OTHER INFORMATION: 1,4-diaminobutane linked between C-terminal
      of Ser 2 and delta C-terminal of Glu 3
<220> FEATURE:
<221> NAME/KEY: MISC_FEATURE
<222> LOCATION: 3..4
<223> OTHER INFORMATION: Alpha carboxylic acid of Glu 3 is linked to NH2
      group of Ser 4
<220> FEATURE:
<221> NAME/KEY: MISC_FEATURE
<222> LOCATION: 7
<223> OTHER INFORMATION: C-terminal of Ser 7 is modified NH2 group
```

```
<400> SEQUENCE: 19

Phe Ser Glu Ser Thr Asn Ser
1               5

<210> SEQ ID NO 20
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1
<223> OTHER INFORMATION: CH3(CH2)8CO- is linked to hydroxy group of Ser
      1
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 20

Ser Asn Thr Ser Glu Phe Ser
1               5

<210> SEQ ID NO 21
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1..2
<223> OTHER INFORMATION: (-CONH-) bond between Ser 1 and Asn 2 is
      reduced to (-CH2NH-)
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 21

Ser Asn Thr Ser Glu Phe Ser
1               5

<210> SEQ ID NO 22
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1..2
<223> OTHER INFORMATION: (-CONH-) bond between Ser 1 and Asn 2 is
      reduced to (-CH2N-) and this reduced amide is substituted with
      CH3(CH2)8CO-
<220> FEATURE:
<221> NAME/KEY: MISC_FEATURE
<222> LOCATION: 5
<223> OTHER INFORMATION: Alpha C-terminal of Glu 5 is modified with NH2
```

```
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 22

Ser Asn Thr Ser Glu Phe Ser
1               5

<210> SEQ ID NO 23
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1..2
<223> OTHER INFORMATION: (-CONH-) bond between Ser 1 and Asn 2 is
      reduced to (-CH2N-) and this reduced amide is substituted with
      CH3(CH2)4CO-
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 23

Ser Asn Thr Ser Glu Phe Ser
1               5

<210> SEQ ID NO 24
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1..2
<223> OTHER INFORMATION: (-CONH-) bond between Ser 1 and Asn 2 is
      reduced to (-CH2N-) and this reduced amide is substituted with
      CH3CO-
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 24

Ser Asn Thr Ser Glu Phe Ser
1               5

<210> SEQ ID NO 25
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 2..3
<223> OTHER INFORMATION: (-CONH-) bond between Asn 2 and Thr 3 is
      reduced to (-CH2NH-)
```

```
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 25

Ser Asn Thr Ser Glu Phe Ser
1               5

<210> SEQ ID NO 26
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 2..3
<223> OTHER INFORMATION: (-CONH-) bond between Asn 2 and Thr 3 is
      reduced to (-CH2N-) and this reduced amide is substituted with
      CH3CO-
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 26

Ser Asn Thr Ser Glu Phe Ser
1               5

<210> SEQ ID NO 27
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 2..3
<223> OTHER INFORMATION: (-CONH-) bond between Asn 2 and Thr 3 is
      reduced to (-CH2N-) and this reduced amide is substituted with
      (CH3)2CHCH2CH2OCO-
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 27

Ser Asn Thr Ser Glu Phe Ser
1               5

<210> SEQ ID NO 28
<211> LENGTH: 7
<212> TYPE: PRT
<213> ORGANISM: Artificial sequence
```

-continued

```
<220> FEATURE:
<223> OTHER INFORMATION: Synthetic Peptide
      220>
<221> NAME/KEY: MISC_FEATURE
<222> LOCATION: 1..2
<223> OTHER INFORMATION: (-CONH-) bond between Ser 1 and Asn 2 is
      reduced to (-CH2N-) and this reduced amide is substituted with
      (CH3)2CHCH2CH2OCO-
<220> FEATURE:
<221> NAME/KEY: MISC_FEATURE
<222> LOCATION: 5
<223> OTHER INFORMATION: Alpha C-terminal of Glu 5 is modified with NH2
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 28

Ser Asn Thr Ser Glu Phe Ser
1               5

<210> SEQ ID NO 29
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 4..5
<223> OTHER INFORMATION: N-terminal of Glu 5 is bonded to C-terminal of
      Ser 4
<220> FEATURE:
<221> NAME/KEY: MISC_FEATURE
<222> LOCATION: 5,6
<223> OTHER INFORMATION: 1,4-diaminobutane linked between delta C-
      terminal of Glu 5 and C-terminal of Phe 6

<400> SEQUENCE: 29

Ser Asn Thr Ser Glu Phe Ser
1               5

<210> SEQ ID NO 30
<211> LENGTH: 7
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 4..5
<223> OTHER INFORMATION: N-terminal of Glu 5 is bonded to C-terminal of
      Ser 4
<220> FEATURE:
<221> NAME/KEY: MISC_FEATURE
<222> LOCATION: 5..6
<223> OTHER INFORMATION: 2,6-diaminohexanoic acid is linked between
      delta C-terminal of Glu 5 and N-terminal of Phe 6
<220> FEATURE:
<221> NAME/KEY: MISC_FEATURE
<222> LOCATION: 7
<223> OTHER INFORMATION: C-terminal of Ser 7 is modified NH2

<400> SEQUENCE: 30

Ser Asn Thr Ser Glu Phe Ser
1               5

<210> SEQ ID NO 31
<211> LENGTH: 6
<212> TYPE: PRT
<213> ORGANISM: Artificial sequence
```

```
<220> FEATURE:
<223> OTHER INFORMATION: Synthetic Peptide
<220> FEATURE:
<221> NAME/KEY: MISC_FEATURE
<222> LOCATION: 3..4
<223> OTHER INFORMATION: N-terminal of Glu 4 is bonded to C-terminal of
      Ser 3
<220> FEATURE:
<221> NAME/KEY: MISC_FEATURE
<222> LOCATION: 4..5
<223> OTHER INFORMATION: 2,6-diaminohexanoic acid is linked between
      delta C-terminal of Glu 4 and N-terminal of Phe 5
<220> FEATURE:
<221> NAME/KEY: MISC_FEATURE
<222> LOCATION: 6
<223> OTHER INFORMATION: C-terminal of Ser 6 is modified NH2

<400> SEQUENCE: 31

Asn Thr Ser Glu Phe Ser
1               5

<210> SEQ ID NO 32
<211> LENGTH: 5
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 2..3
<223> OTHER INFORMATION: N-terminal of Glu 3 is bonded to C-terminal of
      Ser 2
<220> FEATURE:
<221> NAME/KEY: MISC_FEATURE
<222> LOCATION: 3..4
<223> OTHER INFORMATION: 2,6-diaminohexanoic acid is linked between
      delta C-terminal of Glu 3 and N-terminal of Phe 4
<220> FEATURE:
<221> NAME/KEY: MISC_FEATURE
<222> LOCATION: 5
<223> OTHER INFORMATION: C-terminal of Ser 5 is modified NH2

<400> SEQUENCE: 32

Thr Ser Glu Phe Ser
1               5

<210> SEQ ID NO 33
<211> LENGTH: 4
<212> TYPE: PRT
<213> ORGANISM: Artificial sequence
<220> FEATURE:
<223> OTHER INFORMATION: Synthetic Peptide
<220> FEATURE:
<221> NAME/KEY: MISC_FEATURE
<222> LOCATION: 1..2
<223> OTHER INFORMATION: N-terminal of Glu 2 is bonded to C-terminal
      of Ser 1
<220> FEATURE:
<221> NAME/KEY: MISC_FEATURE
<222> LOCATION: 2..3
<223> OTHER INFORMATION: 2,6-diaminohexanoic acid is linked between
      delta C-terminal of Glu 2 and N-terminal of Phe 3
<220> FEATURE:
<221> NAME/KEY: MISC_FEATURE
<222> LOCATION: 4
<223> OTHER INFORMATION: C-terminal of Ser 4 is modified NH2

<400> SEQUENCE: 33

Ser Glu Phe Ser
1
```

The invention claimed is:

1. A peptide derivative of formula (I),

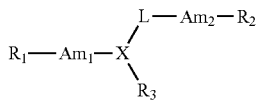 (I)

wherein, $Am_1$ represents 1 to 4 amino acid residues which may be same or different and each independently selected from Ser, Asn and Thr; wherein one of the peptide bond (—CONH—) between any two amino acid residues may be replaced with a modified peptide bond of

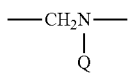

wherein Q is hydrogen, —CO($C_1$-$C_{20}$)alkyl or —COO ($C_1$-$C_{20}$)alkyl;

$Am_2$ is comprising of dipeptide selected from Ser-Phe or Phe-Ser, wherein Phe may be optionally substituted with amino($C_1$-$C_{20}$)alkyl, —NHCOCH$_3$ or —NHCONH$_2$;

X is Glu which may optionally form amide bonds with its alpha carboxylic acid group, delta carboxylic acid group or amino group;

L is a linker selected from —NH(CH$_2$)$_n$NH—, —NH(CH$_2$)$_n$CH(NH$_2$)CO—, —OOC(CH$_2$)$_m$COO—, —NH(CH$_2$)$_n$CO—, —NH(CH$_2$CH$_2$O)$_n$NH—, —NH(CH$_2$CH$_2$O)$_n$CO— or —CO(CH$_2$CH$_2$O)$_n$CO—;

$R_1$ is free C-terminal, amidated C-terminal or N-terminal of $Am_1$; or is ($C_1$-$C_{20}$)acyl substitution;

$R_2$ is free C-terminal, amidated C-terminal or N-terminal of $Am_2$; or Y—$R_5$;

Y is an optional linker selected from —OOC(CH$_2$)$_m$COO—, —CO(CH$_2$)$_n$NH—, —CO(CH$_2$CH$_2$O)$_n$NH— or —COCH$_2$(OCH$_2$CH$_2$)$_n$NH—;

$R_5$ is an albumin binding moiety such as maleimido propionic acid;

$R_3$ is free alpha C-terminal, amidated alpha C-terminal or N-terminal of Glu;

'n' is an integer selected from 2 to 10, both inclusive;

'm' is an integer selected from 0 to 8, both inclusive; wherein one or more or all amino acids may be in a D-configuration;

or its retro analogue or a pharmaceutically acceptable stereoisomer or a pharmaceutically acceptable salt thereof.

2. A peptide derivative of claim 1 having the formula (Ia):

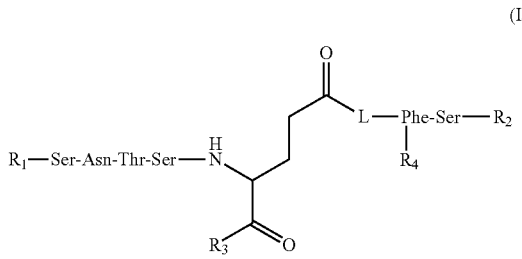 (Ia)

wherein, $R_1$ is N-terminal of Ser; or ($C_1$-$C_{20}$)acyl substituted with either hydroxyl group or amino group of Ser L is a linker selected from —NH(CH$_2$)$_n$NH—, —NH(CH$_2$)$_n$CH(NH$_2$)CO—, —OOC(CH$_2$)$_m$COO—, —NH(CH$_2$)$_n$CO—, —NH(CH$_2$CH$_2$O)$_n$NH—, —NH(CH$_2$CH$_2$O)$_n$CO— or —CO(CH$_2$CH$_2$O)$_n$CO—;

$R_2$ is free C-terminal, amidated C-terminal or N-terminal of $Am_2$; or Y—$R_5$;

Y is an optional linker selected from —OOC(CH$_2$)$_m$COO—, —CO(CH$_2$)$_n$NH—, —CO(CH$_2$CH$_2$O)$_n$NH— or —COCH$_2$(OCH$_2$CH$_2$)$_n$NH—;

$R_5$ is an albumin binding moiety such as maleimido propionic acid;

$R_3$ is OH or NH$_2$;

$R_4$ is a substituent on phenyl group of Phe and is selected from hydrogen, amino($C_1$-$C_{20}$)alkyl, —NHCOCH$_3$ or —NHCONH$_2$;

'n' is an integer having values selected from 2 to 10, both inclusive;

'm' is an integer having values selected from 0 to 8, both inclusive; and one of the peptide bond (—CONH—) of Ser-Asn, Asn-Thr or Thr-Ser may be replaced with a modified peptide bond of

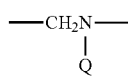

wherein Q is hydrogen, —CO($C_1$-$C_{20}$)alkyl or —COO ($C_1$-$C_{20}$)alkyl group; wherein one or more or all amino acids may be in the D-configuration;

or retro analogue or a pharmaceutically acceptable stereoisomer or a pharmaceutically acceptable salt thereof.

3. The compound according to claim 2, wherein one or more or all amino acids are in the D-configuration.

4. The compound according to claim 2, wherein L is —NH(CH$_2$)$_4$NH—.

5. The compound according to claim 2, wherein L is —NH(CH$_2$)$_4$CH(NH$_2$)CO—.

6. The compound according to claim 2, wherein $R_2$ is N-terminal of Ser.

7. The compound according to claim 2, wherein the peptide bond (—CONH—) of Ser-Asn is replaced with a modified peptide bond of

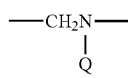

wherein Q is hydrogen, —CO($C_1$-$C_{20}$)alkyl or —COO($C_1$-$C_{20}$)alkyl group.

8. The compound according to claim 2, wherein the peptide bond (—CONH—) of Asn-Thr is replaced with a modified peptide bond of

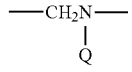

wherein Q is hydrogen, —CO($C_1$-$C_{20}$)alkyl or —COO($C_1$-$C_{20}$)alkyl group.

9. A peptide derivative of claim 1 having the formula (Ib):

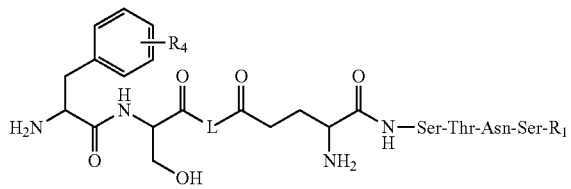

wherein,
R₁ is free C-terminal or amidated C-terminal of Ser;
L is a linker selected from —NH(CH₂)$_n$NH— or —NH(CH₂CH₂O)$_n$NH—;
R₄ is selected from hydrogen, amino(C₁-C₂₀)alkyl, —NHCOCH₃ or —NHCONH₂;
wherein one or more or all amino acids may be in D-configuration;
or retro analogue or a pharmaceutically acceptable stereoisomer or a pharmaceutically acceptable salt thereof.

10. The compound according to claim 9, wherein one or more or all amino acids are in D-configuration.

11. The compound according to claim 9, wherein L is —NH(CH₂)₄NH—.

12. The compound according to claim 9, wherein R₁ is amidated C-terminal of Ser.

13. A compound selected from

| Comp No. | Structure |
|---|---|
| 001 | 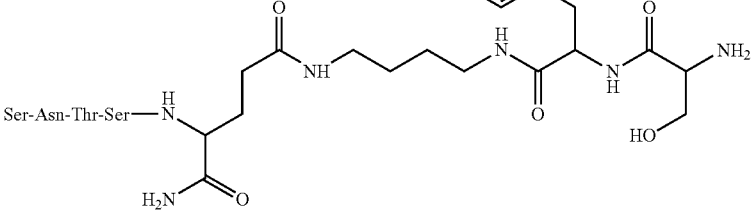<br>(SEQ ID NO: 3) |
| 002 | 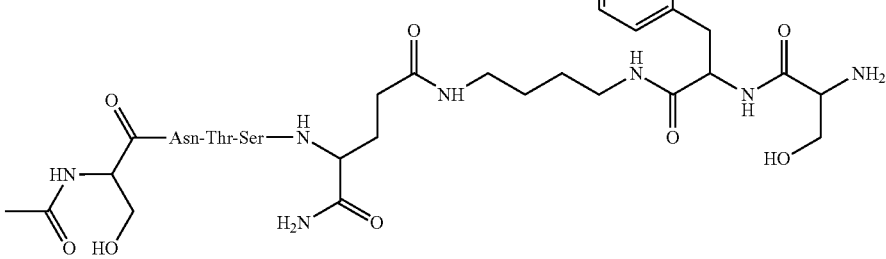<br>(SEQ ID NO: 4) |
| 003 | 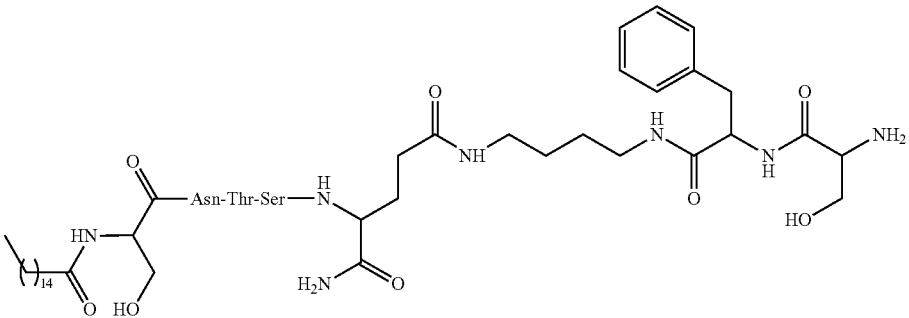<br>(SEQ ID NO: 5) |

| Comp No. | Structure |
|---|---|
| 004 | 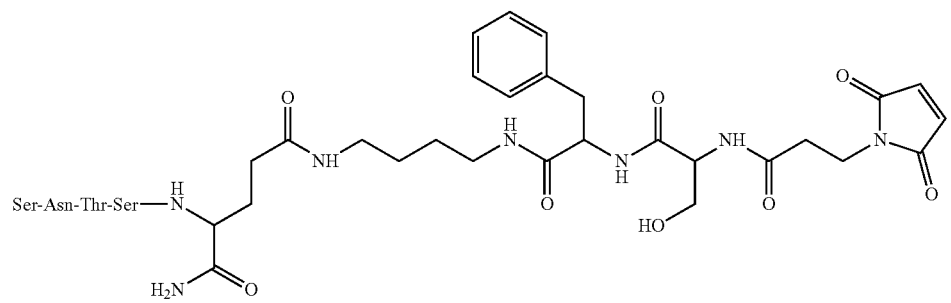<br>(SEQ ID NO: 6) |
| 005 | 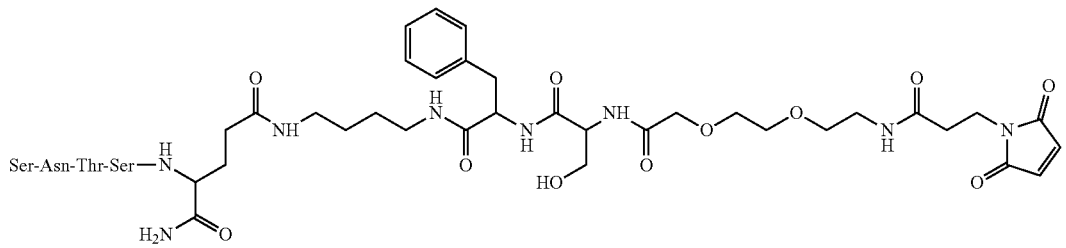<br>(SEQ ID NO: 7) |
| 006 | 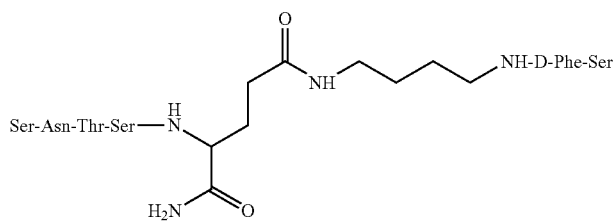<br>(SEQ ID NO: 8) |
| 007 | 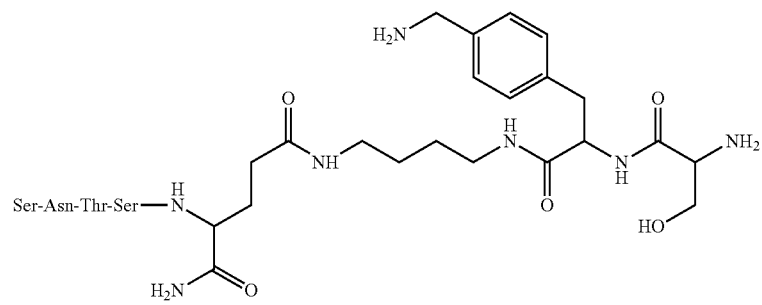<br>(SEQ ID NO: 9) |

-continued
| Comp No. | Structure |
|---|---|
| 008 | 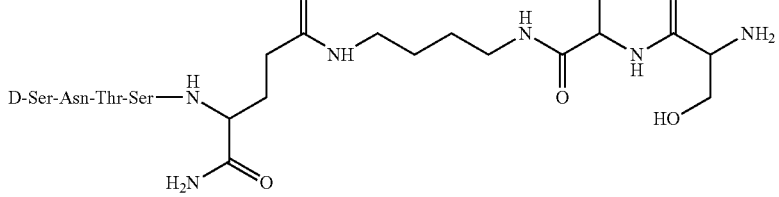<br>(SEQ ID NO: 10) |
| 009 | 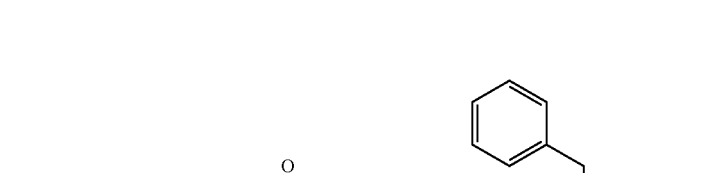<br>(SEQ ID NO: 11) |
| 010 | 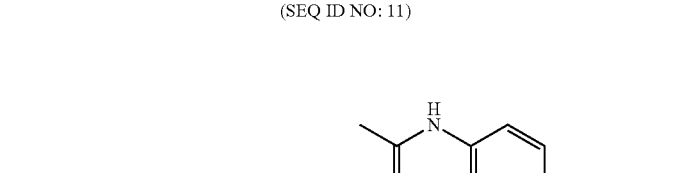<br>*D-Phe<br>(SEQ ID NO: 12) |
| 011 | 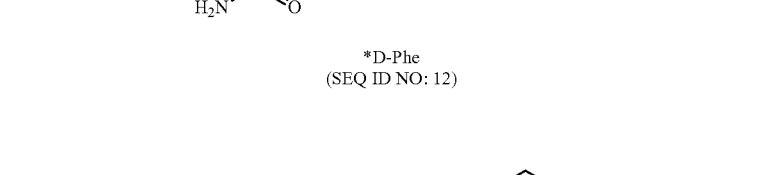<br>(SEQ ID NO: 13) |

| Comp No. | Structure |
|---|---|
| 012 | 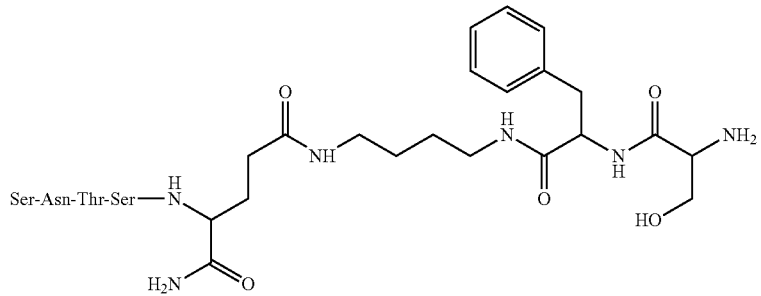<br>*D-Glu<br>(SEQ ID NO: 14) |
| 013 | 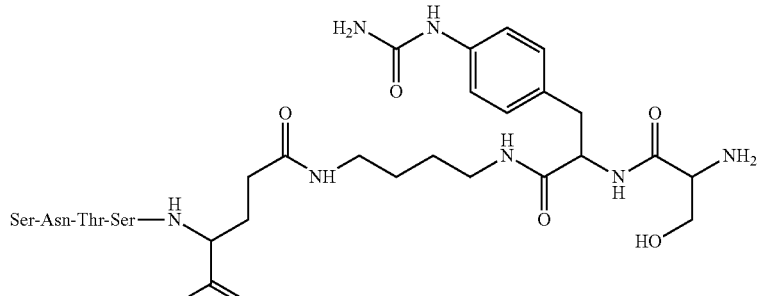<br>*D-Phe urea<br>(SEQ ID NO: 15) |
| 014 | 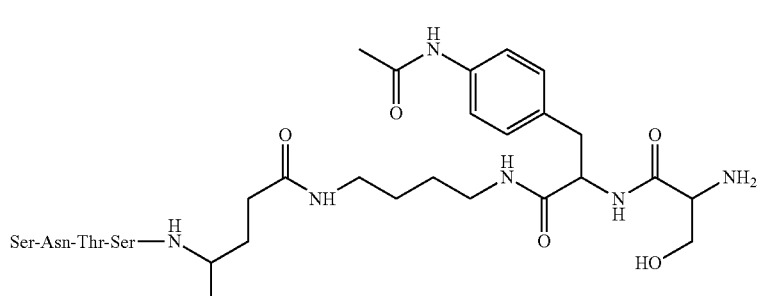<br>(SEQ ID NO: 16) |
| 015 | 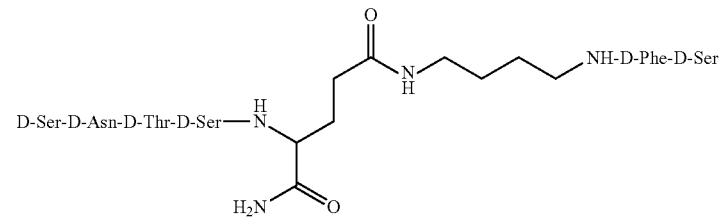<br>*D-Glu<br>(SEQ ID NO: 17) |

| Comp No. | Structure |
|---|---|
| 016 | 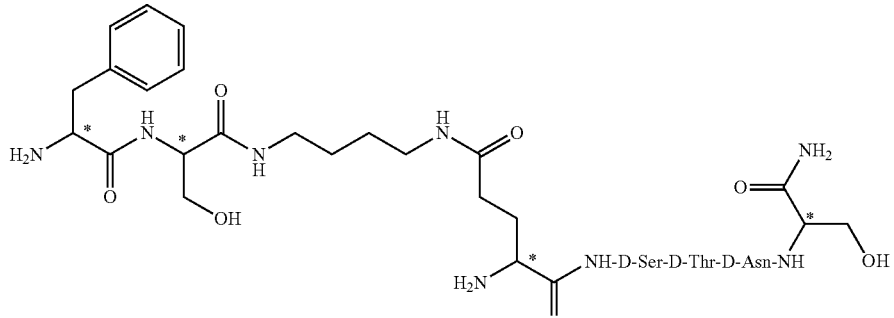<br>*All D-amino acids<br>(SEQ ID NO: 18) |
| 017 | 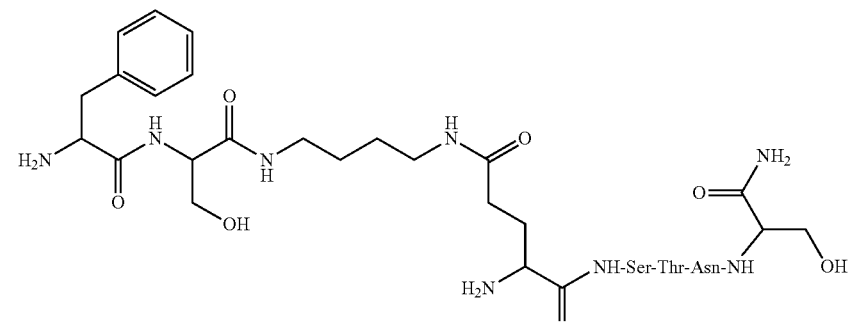<br>(SEQ ID NO: 19) |
| 018 | 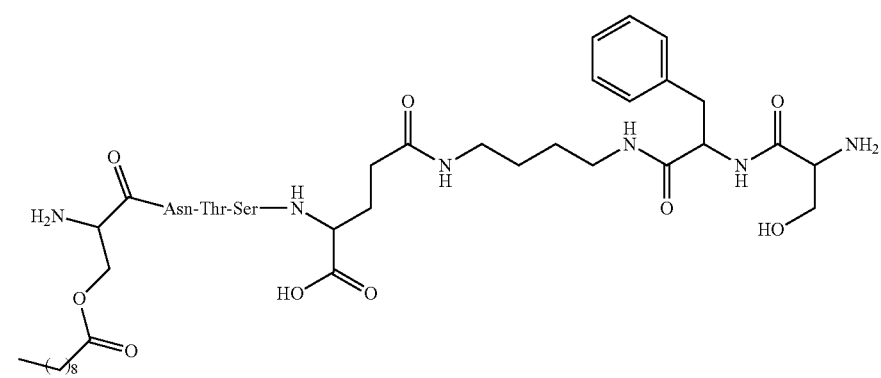<br>(SEQ ID NO: 20) |

| Comp No. | Structure |
|---|---|
| 019 | 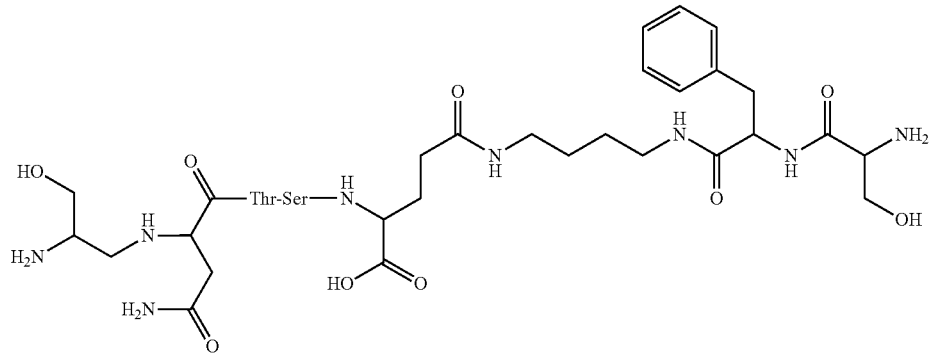<br>(SEQ ID NO: 21) |
| 020 | 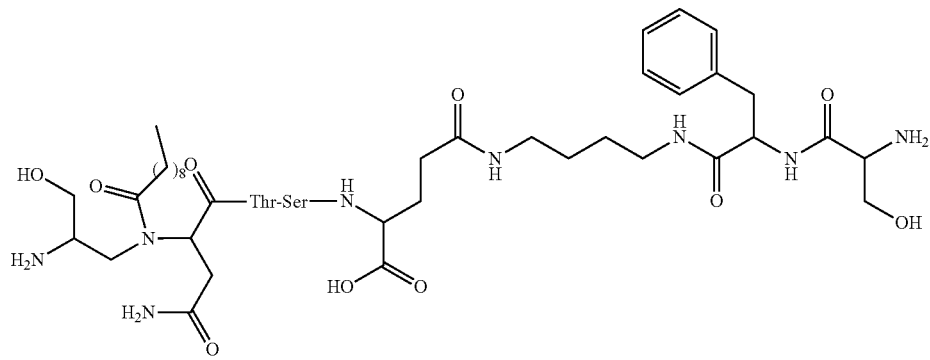<br>(SEQ ID NO: 22) |
| 021 | 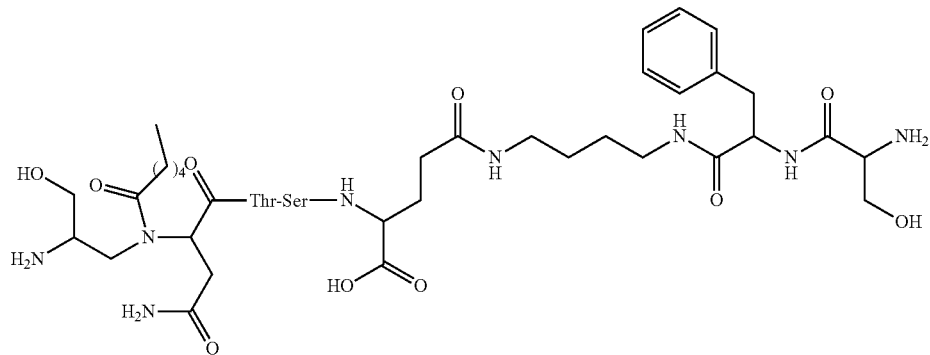<br>(SEQ ID NO: 23) |

| Comp No. | Structure |
|---|---|
| 022 | 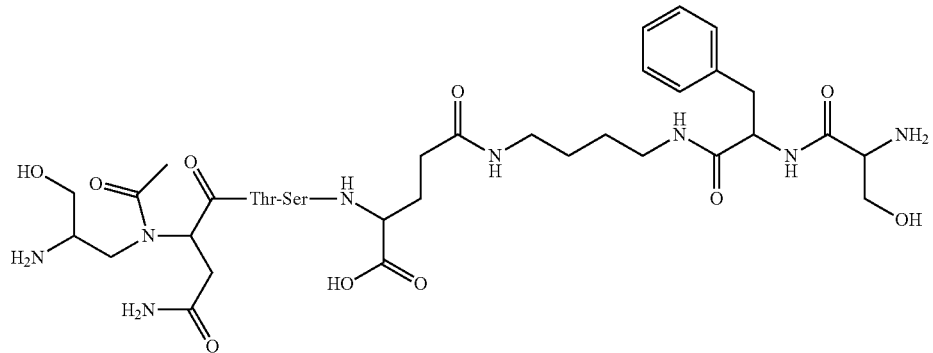<br>(SEQ ID NO: 24) |
| 023 | 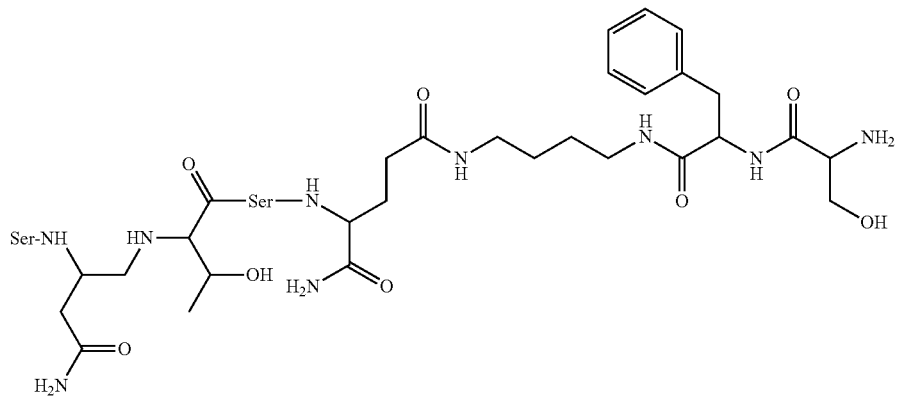<br>(SEQ ID NO: 25) |
| 024 | 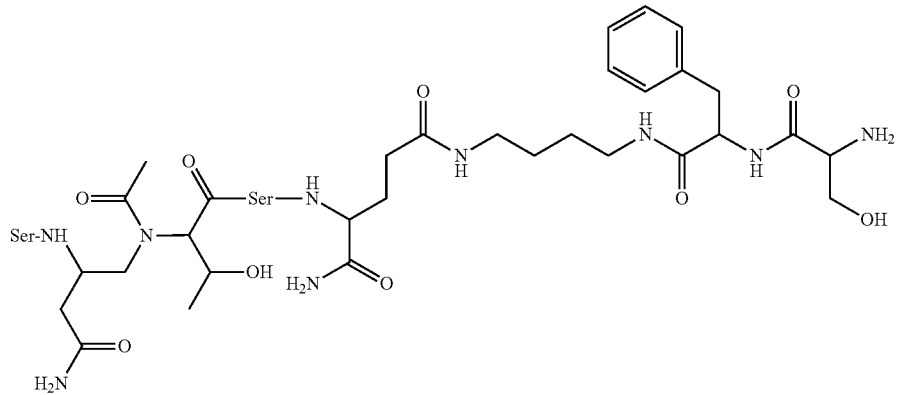<br>(SEQ ID NO: 26) |

| Comp No. | Structure |
|---|---|
| 025 | 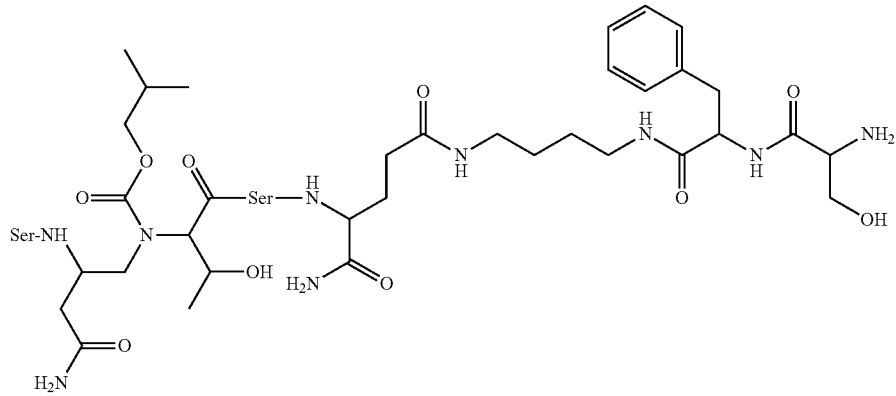<br>(SEQ ID NO: 27) |
| 026 | 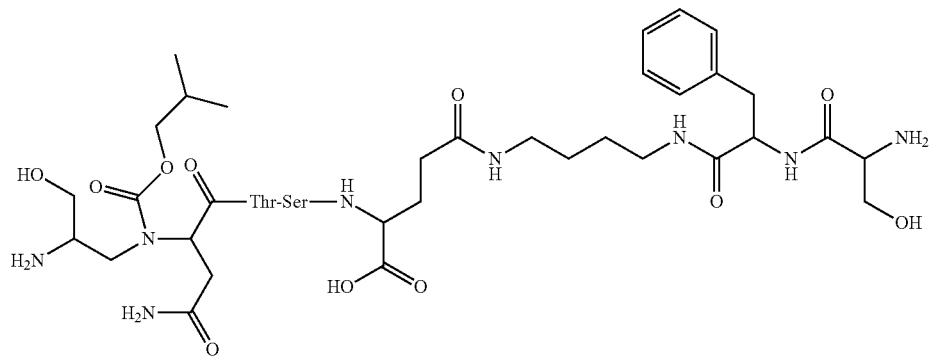<br>(SEQ ID NO: 28) |
| 027 | 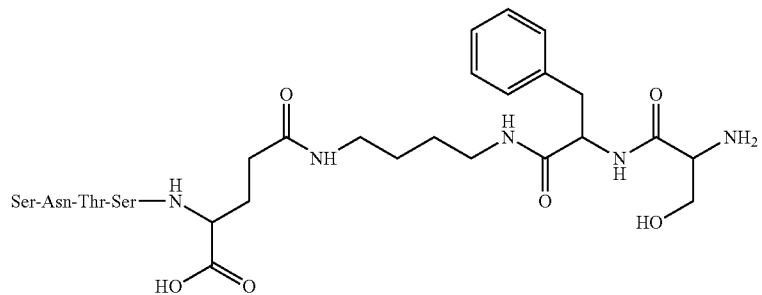<br>(SEQ ID NO: 29) |
| 028 | 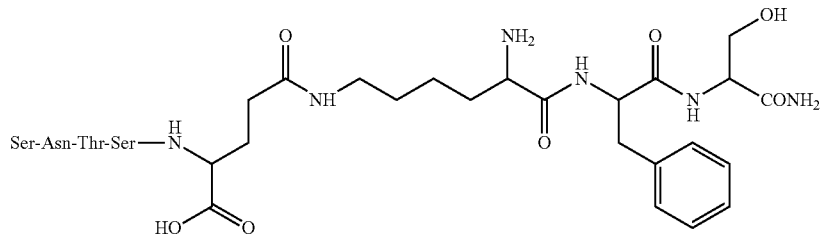<br>(SEQ ID NO: 30) |

| Comp No. | Structure |
|---|---|
| 029 | Asn-Thr-Ser—NH—...—(SEQ ID NO: 31) |
| 030 | Thr-Ser—NH—...—(SEQ ID NO: 32) |
| 031 | Ser—NH—...—(SEQ ID NO: 33) |

14. A compound according to claim 1, for use as a medicament for the treatment of cancer or infectious disease.

15. A pharmaceutical composition comprising a compound according to claim 1, and a pharmaceutically acceptable diluent or carrier.

16. method of inhibiting growth of tumour cells and/or metastasis in a subject, comprising administering to the subject a therapeutically effective amount of compound according to claim 1, capable of inhibiting the programmed cell death 1 (PD1) signaling pathway.

17. The method of claim 16, wherein the tumour cells are of a cancer selected from the group consisting of melanoma, renal cancer, prostate cancer, breast cancer, colon cancer and lung cancer.

18. A method of treating an infectious disease in a subject comprising administering to the subject a therapeutically effective amount of compound according to claim 1, capable of inhibiting the programmed cell death 1 (PD1) signaling pathway such that the subject is treated for the infectious disease.

19. A method of treating bacterial and viral infections in a subject comprising administering to the subject a therapeutically effective amount of compound according to claim 1, capable of inhibiting the programmed cell death 1 (PD1) signaling pathway such that the subject is treated for the bacterial, fungal and viral infections.

20. A method for treating sepsis in a subject comprising administering to the subject a therapeutically effective amount of compound according to claim 1, capable of inhibiting the programmed cell death 1 (PD1) signaling pathway such that the subject is treated for the bacterial, fungal and viral infections.

* * * * *